(12) United States Patent
DeLuca et al.

(10) Patent No.: US 8,143,238 B2
(45) Date of Patent: Mar. 27, 2012

(54) METHODS OF INCREASING EPIDERMAL SKIN THICKNESS BY TOPICAL ADMINISTRATION OF A 19-NOR CONTAINING VITAMIN D COMPOUND

(75) Inventors: Hector F. DeLuca, Deerfield, WI (US); Margaret Clagett-Dame, Deerfield, WI (US); Lori A. Plum, Arena, WI (US); Nirca J. Nieves, Madison, WI (US); Jamie Ahrens, Mount Horeb, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 256 days.

(21) Appl. No.: 12/399,070

(22) Filed: Mar. 6, 2009

(65) Prior Publication Data

US 2009/0227545 A1    Sep. 10, 2009

Related U.S. Application Data

(60) Provisional application No. 61/034,401, filed on Mar. 6, 2008.

(51) Int. Cl.
*A61K 31/59* (2006.01)
*C07D 401/00* (2006.01)
(52) U.S. Cl. ........................ 514/167; 552/653
(58) Field of Classification Search .......... 514/167; 552/653
See application file for complete search history.

(56) References Cited

U.S. PATENT DOCUMENTS

| 6,392,071 B1 | 5/2002 | DeLuca et al. |
| 6,566,352 B1 | 5/2003 | DeLuca et al. |
| 2005/0119242 A1 | 6/2005 | DeLuca et al. |
| 2007/0191316 A1 | 8/2007 | Deluca et al. |

FOREIGN PATENT DOCUMENTS

| WO | 0220021 A | 3/2002 |
| WO | 03051828 A | 6/2003 |
| WO | 2006057913 A | 6/2006 |
| WO | 2006057917 A | 6/2006 |
| WO | 2006086608 A | 8/2006 |

(Continued)

OTHER PUBLICATIONS

Baumann, "Skin ageing and its treatment." J. Pathology (2007) 211:241-251.

(Continued)

*Primary Examiner* — Sabiha Qazi
(74) *Attorney, Agent, or Firm* — Quarles & Brady, LLP

(57) ABSTRACT

Methods of increasing the thickness of the epidermal layer in the skin of a human comprising topically administering a therapeutically effective dose of an active pharmaceutical ingredient comprising a vitamin D analog including 2-methylene-19-nor-20(S)-1α-hydroxy-bishomopregnacalciferol, 19-nor-26,27-dimethylene-20(S)-2-methylene-1α,25-dihydroxyvitamin $D_3$, 2-methylene-19-nor-(24R)-1α,25-dihydroxyvitamin $D_2$, 2-methylene-1α,25-dihydroxy-(17E)-17 (20)-dehydro-19-nor-vitamin $D_3$, 2-methylene-(20R,25S)-19,26-dinor-1α,25-dihydroxyvitamin $D_3$, 2-methylene-18,19-dinor-(20S)-1α,25-dihydroxyvitamin $D_3$, 2-methylene-19-nor-1α-hydroxy-pregnacalciferol, 1α-hydroxy-2-methylene-19-nor-homopregnacalciferol, (20R)-1α-hydroxy-2-methylene-19-nor-bishomopregnacalciferol, 2-methylene-(20S)-19-nor-1α-hydroxy-trishomopregnacalciferol, 2-methylene-(20R)-23,23-difluoro-1α-hydroxy-19-nor-bishomopregnacalciferol, 2-methylene-(20S)-23,23-difluoro-1α-hydroxy-19-nor-bishomopregnacalciferol, 2-(3'hydroxypropyl-1',2'-idene)-19,23,24-trinor-(20S)-1α-hydroxyvitamin $D_3$, or 13,13-dimethyl-des-C,D analog of (20S)-2-methylene-1α,25-dihydroxy-19-nor-vitamin $D_3$, and pharmaceutical topical formulations and topical dosage forms thereof using a pharmaceutically suitable carrier vehicle.

29 Claims, 11 Drawing Sheets

FOREIGN PATENT DOCUMENTS

Figure 1:
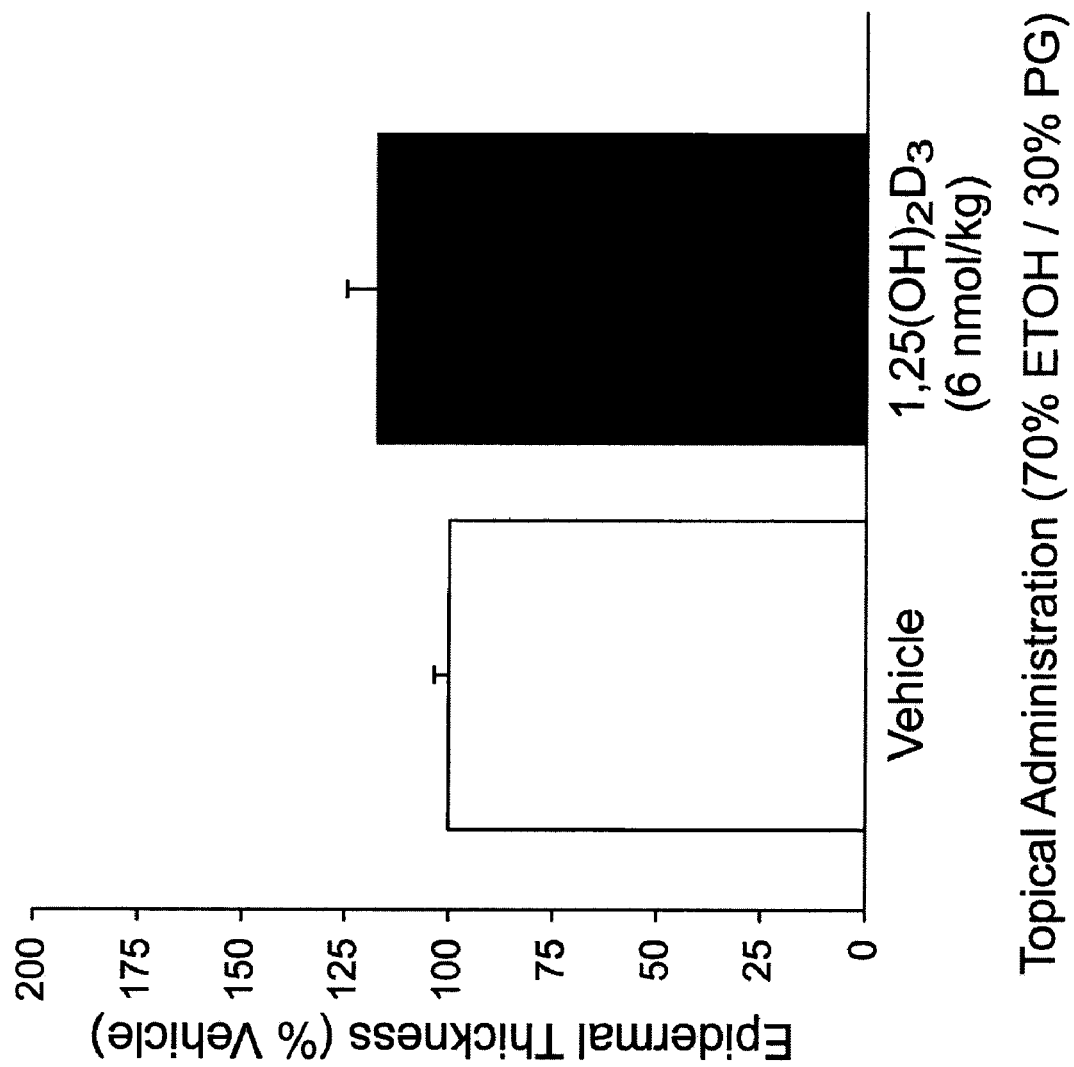

| | | |
|---|---|---|
| WO | 2007117563 A | 10/2007 |
| WO | 2008083370 A | 7/2008 |

OTHER PUBLICATIONS

Chebotaev et al., "Epithelial cells in the hair follicle bulge do not contribute to epidermal regeneration after glucocorticoid-induced cutaneous atrophy." J Invest Dermatol (2007) 127:2749-2758.

Gambichler et al., "In vivo data of epidermal thickness evaluated by optical coherence tomography: Effects of age, gender, skin type, and anatomic site." J. Dermatol. Sci. (2006) 44:145-152.

Gniadecki et al., "Stimulation of epidermal proliferation in mice with 1alpha,25dihydroxyvitamin D3 and receptor-active 20-epi analogues of 1alpha,25-dihydroxyvitamin D3." Biochem. Pharmacol. (1995) 49:621-624.

Hosomi et al., "Regulation of terminal differentiation of cultured mouse epidermal cells by 1alpha,25-dihydroxyvitamin D3." Endocrinology (1983) 113:1950-1957.

Yaar et al., "Photoageing : mechanism, prevention and therapy." Br. J. Dermatology (2007) 157:874-887.

PCT/US2009/036323 International Search Report.

Gniadecki, Robert et al., "Inhibition of glucocorticoid-induced epidermal and dermal atrophy with KH 1060: A potent 20-epi analogue of 1,25-dihydroxyvitamin D-3," British Journal of Phamacology, vol. 113, No. 2, 1994, pp. 439-444.

Von Brenken S. et al., "Topical vitamin D3 derivatives impair the epidermal permeability barrier in normal mouse skin," Dermatology, vol. 194, No. 2, Jan. 1, 1997, pp. 151-156.

Fujimura Tsutomu et al., "Epidermal change can alter mechanical properties of hairless mouse skin topically treated with 1alpha, 25-dihydroxyvitamin D3," Journal of Dermatological Science, vol. 24, No. 2, Nov. 2000, pp. 105-111.

Gurlek A. et al., "Modulation of growth factor/cytokine synthesis and signaling by 1alpha,25-dihydroxyvitamin D3: Implications in cell growth and differentiation," Endocrine Reviews, Baltimore, MD, US, vol. 23, No. 6, Dec. 1, 2002, pp. 763-786.

Lutzow-Holm C et al., "1,25-hydroxyvitamin D3 and the vitamin D analogue KH1060 induce hyperproliferation in normal mouse epidermis. A BrdUrd/DNA flow cytometric study." Experimental Dermatology Jun. 2003, vol. 2, No. 3, Jun. 2003, pp. 113-120.

Vanhooke et al., "New analogs of 2-methylene-19-nor-(20S)-1,25-dihydroxyvitamin D3 with conformationally restricted side chains: Evaluation of biological activity and structural determination of VDR-bound conformations," Archives of Biochemistry and Biophysics, Academics Press, US, vol. 460, No. 2, Apr. 18, 2007, pp. 161-165.

DeLuca et al., "Selective analogs of 1alpha,25-dihydroxyvitamin D3 for the study of specific functions of Vitamin D," Journal of Steroid Biochemistry and Molecular Biology, Elsevier Science Ltd., Oxford, GB, vol. 103, No. 3-5, Mar. 15, 2007, pp. 263-268.

Bikle, "Vitamin D and Skin", Vitamin D, 1997, pp. 386-389, David Feldman, Editor-in-Chief, Academic Press, San Diego, California.

Matsumoto, et al., "Growth-Inhibitory Effects of 1,25-Dihydroxyvitamin D3 on Normal Human Keratinocytes Cultured in Serum-Free Medium", Biochemical and Biophysical Research Communications, 1990, 166(2):916-923.

METHODS OF INCREASING EPIDERMAL SKIN THICKNESS BY TOPICAL ADMINISTRATION OF A 19-NOR CONTAINING VITAMIN D COMPOUND

CROSS REFERENCE TO RELATED APPLICATIONS

This application claims priority to and benefit of U.S. Provisional Patent Application Ser. No. 61/034,401 filed on Mar. 6, 2008.

U.S. patent Nonprovisional patent application Ser. No. 11/966,504 is commonly owned and discloses related subject matter.

STATEMENT REGARDING GOVERNMENT INTEREST

Not applicable.

BACKGROUND OF THE INVENTION

The skin is made up of three layers including the epidermis, dermis and subcutaneous or fat layer. The epidermis of the skin is the outer layer and is a continuously renewing tissue. The majority of cells in the epidermis are keratinocytes that originate in the basal layer. The keratinocytes migrate from the basal layer to the outermost layer known as the stratum corneum.

The epidermis provides a protective barrier against transcutaneous water loss. The epidermis also prevents most bacteria, viruses and other foreign substances from entering the body. The epidermis also protects the internal body from trauma.

The dermis is a layer of fibrous and elastic tissue that provides the skin flexibility and strength. The underlying fat layer provides insulation from heat and cold. The fat layer also provides an energy depot.

When skin ages, the epidermal and dermal layers atrophy. It has been reported in studies that aged skin is characterized by a thinning epidermis. (Gambichler et al., 2006, *J. Dermatological Sci.* 44:145-152). It has also been reported that the epidermal turnover rate slows with aging. (Baumann, 2007, *J. Pathology* 211:241-251). As a result, a protracted rate of stratum corneum replacement occurs. Moreover, epidermal atrophy and slower wound healing can also occur. Often, less effective desquamation is also prevalent. Such decelerated cell turnover can cause the skin surface to appear rough and dull in appearance. In sum, as skin ages it becomes dry, wrinkled and fragile, and a loss of skin barrier function results.

Photoaging superimposes the effect of chronic ultraviolet induced (UV-induced) damage in addition to normal intrinsic skin aging, which leads to further changes in the skin. It has been reported that epidermal atrophy may occur in some individuals. (Yaar et al., 2007, *Br. J. Dermatology* 157:874-887).

In addition to skin aging, treatment using glucocorticoid hormones may inhibit keratinocyte proliferation. However, chronic glucocorticoid hormone treatment is accompanied by side effects including reduced epidermal thickness, decreased number of keratinocytes, and loss of skin barrier function. (Chebotaev et al., 2007, *J. Investigative Dermatology* 127:2749-2758).

SUMMARY OF THE INVENTION

One aspect of the invention is a method of increasing the thickness of the epidermal layer in the skin of a human comprising topically administering a therapeutically effective dose of an active pharmaceutical ingredient comprising 2-methylene-19-nor-20(S)-1α-hydroxy-bishomopregnacalciferol (2MBisP) according to the structure

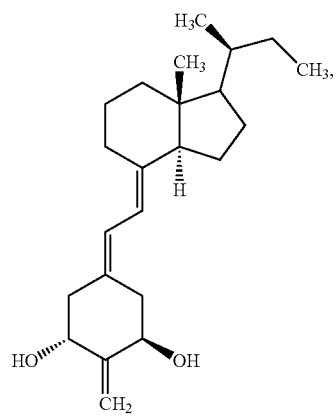

or, a stereoisomer or solute thereof. In an exemplary embodiment, the therapeutically effective dose is in the range of about 340 mg to 0.34 µg/kg$_{BW}$/day.

Another aspect of the invention is a method of increasing the thickness of the epidermal layer in the skin of a human comprising topically administering a therapeutically effective dose of an active pharmaceutical ingredient comprising 19-nor-26,27-dimethylene-20(S)-2-methylene-1α,25-dihydroxyvitamin D$_3$ (CAGE-3) according to the structure

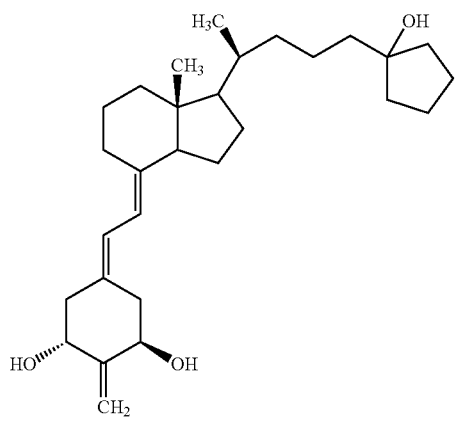

or, a stereoisomer or solute thereof. In an exemplary embodiment, the therapeutically effective dose is in the range of about 14 µg to 14 pg/kg$_{BW}$/day. Another aspect of the invention is a method of increasing the thickness of the epidermal layer in the skin of a human comprising topically administering a therapeutically effective dose of an active pharmaceutical ingredient comprising 2-methylene-19-nor-(24R)-1α,25-dihydroxyvitamin D$_2$ ((24R)2MD$_2$) according to the structure

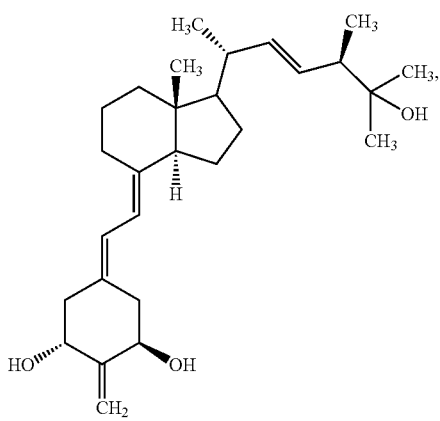

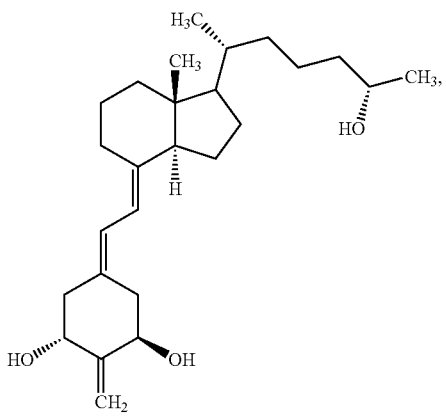

or, a stereoisomer or solute thereof. In an exemplary embodiment, the therapeutically effective dose is in the range of about 450 μg to 0.45 ng/kg$_{BW}$/day.

Another aspect of the invention is a method of increasing the thickness of the epidermal layer in the skin of a human comprising topically administering a therapeutically effective dose of an active pharmaceutical ingredient comprising 2-methylene-1α,25-dihydroxy-(17E)-17(20)-dehydro-19-nor-vitamin D$_3$ (Vit-III (17-20E)) according to the structure or, a stereoisomer or solute thereof. In an exemplary embodiment, the therapeutically effective dose is in the range of about 4.5 mg to 4.5 ng/kg$_{BW}$/day.

Another aspect of the invention is a method of increasing the thickness of the epidermal layer in the skin of a human comprising topically administering a therapeutically effective dose of an active pharmaceutical ingredient comprising 2-methylene-18,19-dinor-(20S)-1α,25-dihydroxyvitamin D$_3$ (VD-03) according to the structure

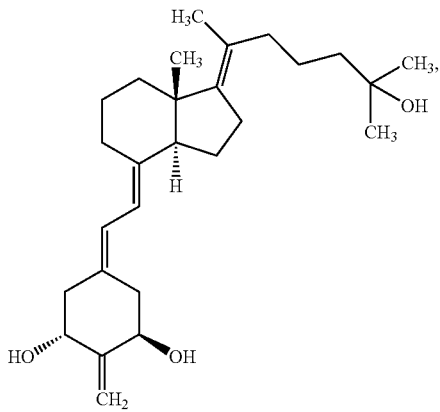

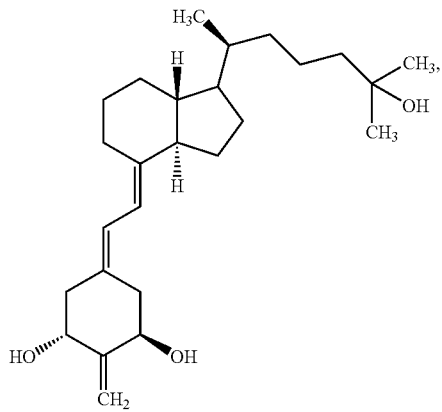

or, a stereoisomer or solute thereof. In an exemplary embodiment, the therapeutically effective dose is in the range of about 4.5 mg to 4.5 ng/kg$_{BW}$/day.

Another aspect of the invention is a method of increasing the thickness of the epidermal layer in the skin of a human comprising topically administering a therapeutically effective dose of an active pharmaceutical ingredient comprising 2-methylene-(20R,25S)-19,26-dinor-1α,25-dihydroxyvitamin D$_3$ (NEL) according to the structure or, a stereoisomer or solute thereof In an exemplary embodiment, the therapeutically effective dose is in the range of about 11 μg to 0.11 ng/kg$_{BW}$/day.

Another aspect of the invention is a method of increasing the thickness of the epidermal layer in the skin of a human comprising topically administering a therapeutically effective dose of an active pharmaceutical ingredient comprising 2-methylene-19-nor-1α-hydroxy-pregnacalciferol (2MPregna) according to the structure

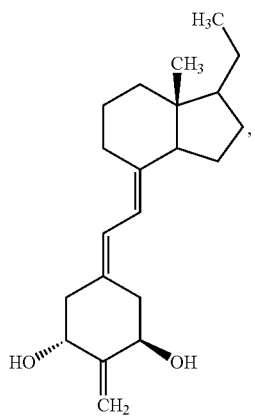

or, a stereoisomer or solute thereof. In an exemplary embodiment, the therapeutically effective dose is in the range of about 340 mg to 0.34 µg/kg$_{BW}$/day.

Another aspect of the invention is a method of increasing the thickness of the epidermal layer in the skin of a human comprising topically administering a therapeutically effective dose of an active pharmaceutical ingredient comprising 1α-hydroxy-2-methylene-19-nor-homopregnacalciferol (2MP) according to the structure

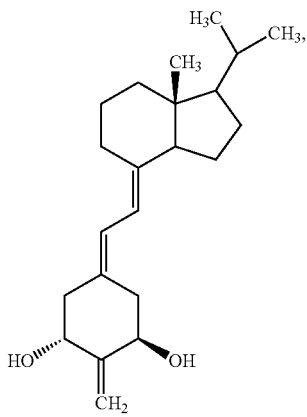

or, a stereoisomer or solute thereof. In an exemplary embodiment, the therapeutically effective dose is in the range of about 340 mg to 0.34 µg/kg$_{BW}$/day.

Another aspect of the invention is a method of increasing the thickness of the epidermal layer in the skin of a human comprising topically administering a therapeutically effective dose of an active pharmaceutical ingredient comprising (20R)-1α-hydroxy-2-methylene-19-nor-bishomopregnacalciferol (20R-2MBisP) according to the structure

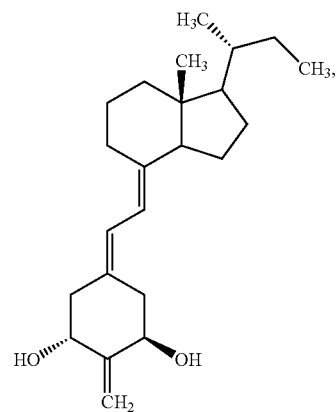

or, a stereoisomer or solute thereof. In an exemplary embodiment, the therapeutically effective dose is in the range of about 340 mg to 0.34 µg/kg$_{BW}$/day.

Another aspect of the invention is a method of increasing the thickness of the epidermal layer in the skin of a human comprising topically administering a therapeutically effective dose of an active pharmaceutical ingredient comprising 2-methylene-(20S)-19-nor-1α-hydroxy-trishomopregnacalciferol (2MTrisP) according to the structure

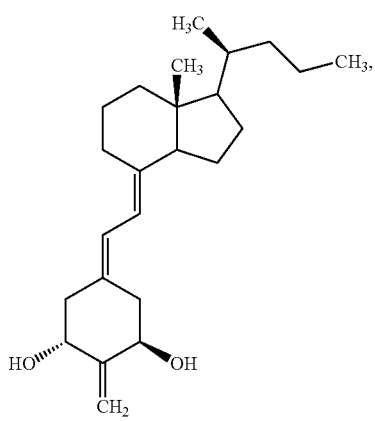

or, a stereoisomer or solute thereof. In an exemplary embodiment, the therapeutically effective dose is in the range of about 34 mg to 34 ng/kg$_{BW}$/day.

Another aspect of the invention is a method of increasing the thickness of the epidermal layer in the skin of a human comprising topically administering a therapeutically effective dose of an active pharmaceutical ingredient comprising 2-methylene-(20R)-23,23-difluoro-1α-hydroxy-19-nor-bishomopregnacalciferol (FF-44) according to the structure

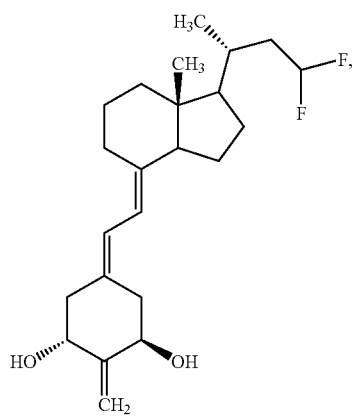

or, a stereoisomer or solute thereof. In an exemplary embodiment, the therapeutically effective dose is in the range of about 340 mg to 0.34 µg/kg$_{BW}$/day.

Another aspect of the invention is a method of increasing the thickness of the epidermal layer in the skin of a human comprising topically administering a therapeutically effective dose of an active pharmaceutical ingredient comprising 2-methylene-(20S)-23,23-difluoro-1α-hydroxy-19-nor-bishomopregnancalciferol (FF-55) according to the structure

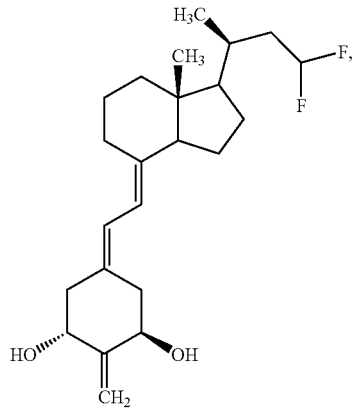

or, a stereoisomer or solute thereof. In an exemplary embodiment, the therapeutically effective dose is in the range of about 340 mg to 0.34 µg/kg$_{BW}$/day.

Another aspect of the invention is a method of increasing the thickness of the epidermal layer in the skin of a human comprising topically administering a therapeutically effective dose of an active pharmaceutical ingredient comprising 2-(3'hydroxypropyl-1',2'-idene)-19,23,24-trinor-(20S)-1α-hydroxyvitamin D$_3$ (HPBS) according to the structure

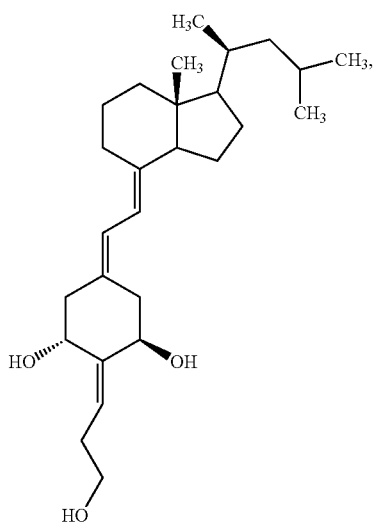

or, a stereoisomer or solute thereof. In an exemplary embodiment, the therapeutically effective dose is in the range of about 41 mg to 41 ng/kg$_{BW}$/day.

Another aspect of the invention is a method of increasing the thickness of the epidermal layer in the skin of a human comprising topically administering a therapeutically effective dose of an active pharmaceutical ingredient comprising 13,13-dimethyl-des-C,D analog of (20S)-2-methylene-1α,25-dihydroxy-19-nor-vitamin D$_3$ (13Me$_2$) according to the structure

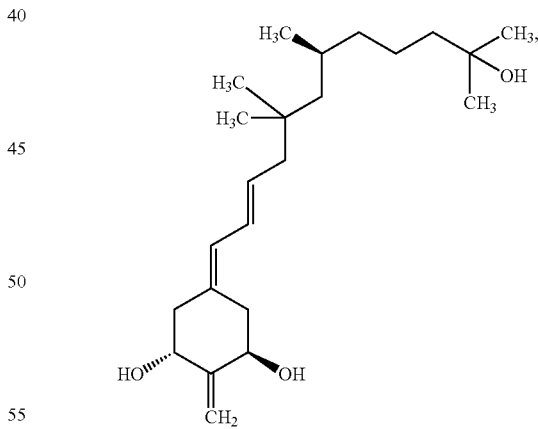

or, a stereoisomer or solute thereof. In an exemplary embodiment, the therapeutically effective dose is in the range of about 36 mg to 36 ng/kg$_{BW}$/day.

Another aspect of the invention is topical dosage form composition comprising a therapeutically effective dose of an active pharmaceutical ingredient comprising 2-methylene-19-nor-20(S)-1α-hydroxy-bishomopregnacalciferol according to the structure

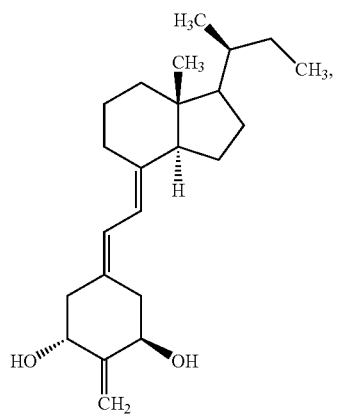

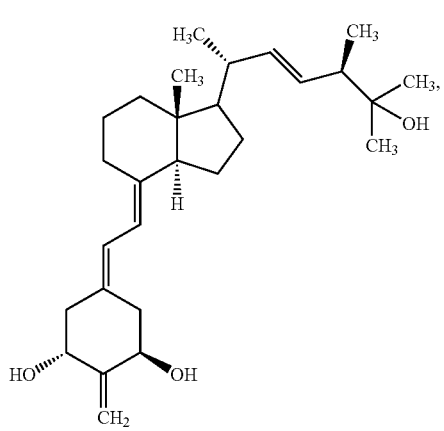

or, a stereoisomer thereof or solute thereof, and, a pharmaceutically suitable carrier vehicle. In an exemplary embodiment, the therapeutically effective dose is in the range of about 340 mg to 0.34 µg/kg$_{BW}$/day.

Another aspect of the invention is a topical dosage form composition comprising a therapeutically effective dose of an active pharmaceutical ingredient comprising 19-nor-26,27-dimethylene-20(S)-2-methylene-1α,25-dihydroxyvitamin D$_3$ according to the structure or, a stereoisomer or solute thereof, and, a pharmaceutically suitable carrier vehicle. In an exemplary embodiment, the therapeutically effective dose is in the range of about 450 µg to 0.45 ng/kg$_{BW}$/day.

Another aspect of the invention is a topical dosage form composition comprising a therapeutically effective dose of an active pharmaceutical ingredient comprising 2-methylene-1α,25-dihydroxy-(17E)-17(20)-dehydro-19-nor-vitamin D$_3$ according to the structure

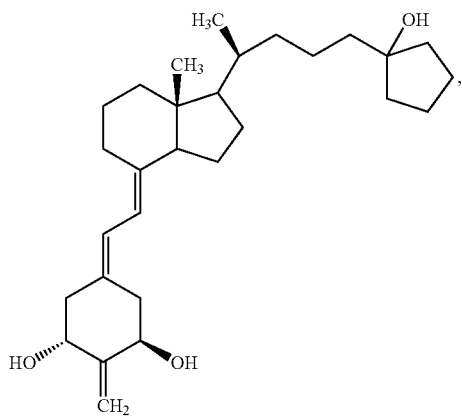

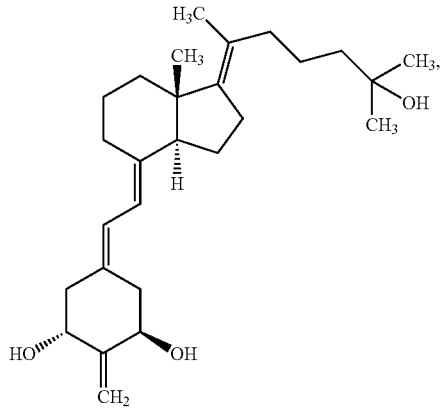

or, a stereoisomer or solute thereof, and, a pharmaceutically suitable carrier vehicle. In an exemplary embodiment, the therapeutically effective dose is in the range of about 14 µg to 14 pg/kg$_{BW}$/day.

Another aspect of the invention is a topical dosage form composition comprising a therapeutically effective dose of an active pharmaceutical ingredient comprising 2-methylene-19-nor-(24R)-1α,25-dihydroxyvitamin D$_2$ according to the structure or, a stereoisomer or solute thereof, and, a pharmaceutically suitable carrier vehicle. In an exemplary embodiment the therapeutically effective dose is in the range of about 4.5 mg to 4.5 ng/kg$_{BW}$/day.

Another aspect of the invention is a topical dosage form composition comprising a therapeutically effective dose of an active pharmaceutical ingredient comprising 2-methylene-(20R,25S)-19,26-dinor-1α,25-dihydroxyvitamin D$_3$ according to the structure

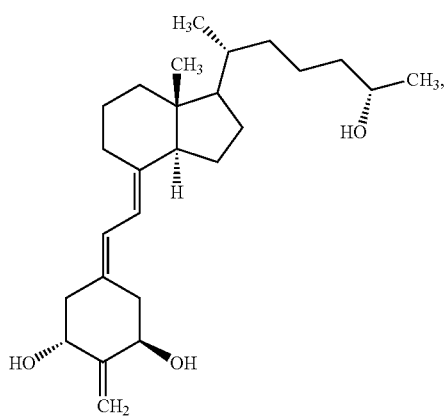

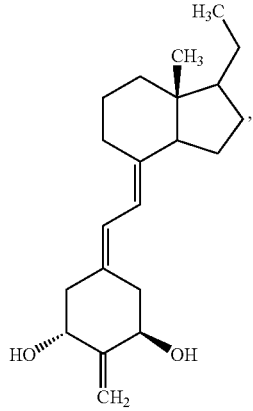

or, a stereoisomer or solute thereof, and, a pharmaceutically suitable carrier vehicle. In an exemplary embodiment, the therapeutically effective dose is in the range of about 4.5 mg to 4.5 ng/kg$_{BW}$/day.

Another aspect of the invention is a topical dosage form composition comprising a therapeutically effective dose of an active pharmaceutical ingredient comprising 2-methylene-18,19-dinor-(20S)-1α,25-dihydroxyvitamin D$_3$ according to the structure or, a stereoisomer or solute thereof, and, a pharmaceutically suitable carrier vehicle. In an exemplary embodiment, the therapeutically effective dose is in the range of about 340 mg to 0.34 μg/kg$_{BW}$/day.

Another aspect of the invention is a topical dosage form composition comprising a therapeutically effective dose of an active pharmaceutical ingredient comprising 1α-hydroxy-2-methylene-19-nor-homopregnacalciferol according to the structure

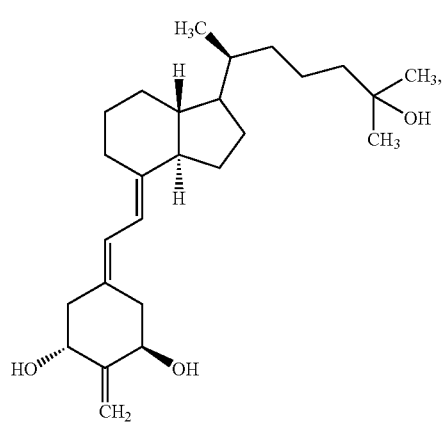

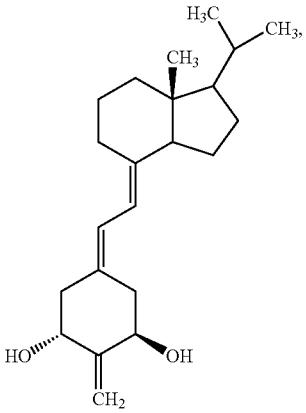

or, a stereoisomer or solute thereof, and, a pharmaceutically suitable carrier vehicle. In an exemplary embodiment, the therapeutically effective dose is in the range of about 11 μg to 0.11 ng/kg$_{BW}$/day.

Another aspect of the invention is a topical dosage form composition comprising a therapeutically effective dose of an active pharmaceutical ingredient comprising 2-methylene-19-nor-1α-hydroxy-pregnacalciferol or, a stereoisomer or solute thereof, and, a pharmaceutically suitable carrier vehicle. In an exemplary embodiment, the therapeutically effective dose is in the range of about 340 mg to 0.34 μg/kg$_{BW}$/day.

Another aspect of the invention is a topical dosage form composition comprising a therapeutically effective dose of an active pharmaceutical ingredient comprising (20R)-1α-hydroxy-2-methylene-19-nor-bishomopregnacalciferol according to the structure

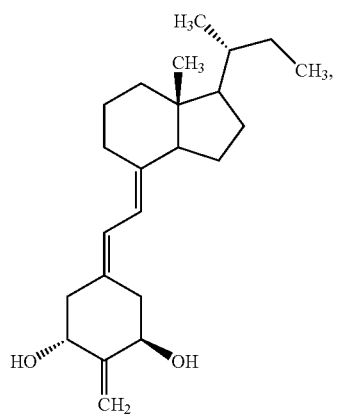

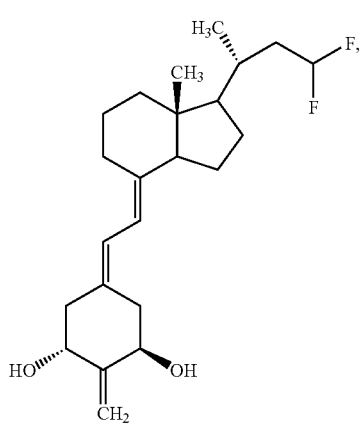

or, a stereoisomer or solute thereof, and, a pharmaceutically suitable carrier vehicle. In an exemplary embodiment, the therapeutically effective dose is in the range of about 340 mg to 0.34 μg/kg$_{BW}$/day.

Another aspect of the invention is a topical dosage form composition comprising a therapeutically effective dose of an active pharmaceutical ingredient comprising 2-methylene-(20S)-19-nor-1α-hydroxy-trishomopregnacalciferol or, a stereoisomer or solute thereof, and, a pharmaceutically suitable carrier vehicle. In an exemplary embodiment, the therapeutically effective dose is in the range of about 340 mg to 0.34 μg/kg$_{BW}$/day.

Another aspect of the invention is a topical dosage form composition comprising a therapeutically effective dose of an active pharmaceutical ingredient comprising 2-methylene-(20S)-23,23-difluoro-1α-hydroxy-19-nor-bishomopregnancalciferol according to the structure

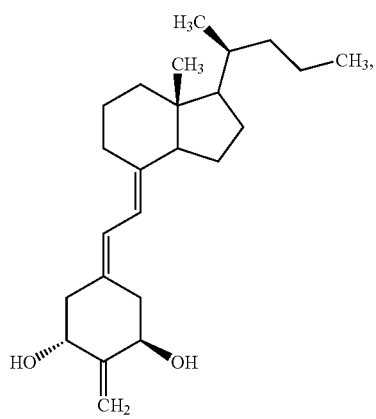

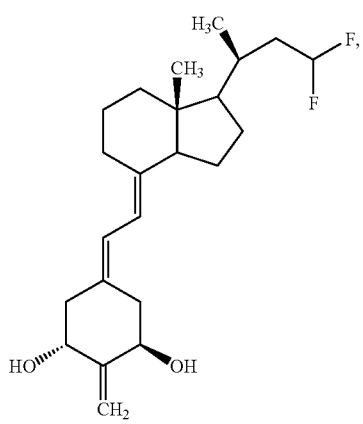

or, a stereoisomer or solute thereof, and, a pharmaceutically suitable carrier vehicle. In an exemplary embodiment, the therapeutically effective dose is in the range of about 34 mg to 34 ng/kg$_{BW}$/day.

Another aspect of the invention is a topical dosage form composition comprising a therapeutically effective dose of an active pharmaceutical ingredient comprising 2-methylene-(20R)-23,23-difluoro-1α-hydroxy-19-nor-bishomopregnacalciferol according to the structure or, a stereoisomer or solute thereof, and, a pharmaceutically suitable carrier vehicle. In an exemplary embodiment, the therapeutically effective dose is in the range of about 340 mg to 0.34 μg/kg$_{BW}$/day.

Another aspect of the invention is a topical dosage form composition comprising a therapeutically effective dose of an active pharmaceutical ingredient comprising 2-(3'hydroxypropyl-1',2'-idene)-19,23,24-trinor-(20S)-1α-hydroxyvitamin D$_3$ according to the structure

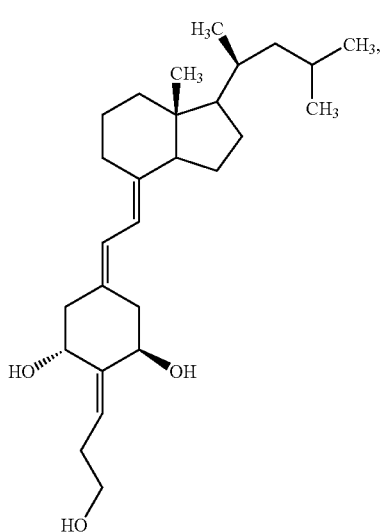

or, a stereoisomer or solute thereof, and, a pharmaceutically suitable carrier vehicle. In an exemplary embodiment, the therapeutically effective dose is in the range of about 41 mg to 41 ng/$kg_{BW}$/day.

Another aspect of the invention is a topical dosage form composition comprising a therapeutically effective dose of an active pharmaceutical ingredient comprising 13,13-dimethyl-des-C,D analog of (20S)-2-methylene-1α,25-dihydroxy-19-nor-vitamin $D_3$ according to the structure

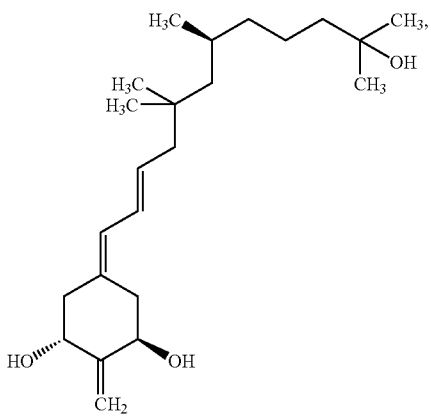

or, a stereoisomer or solute thereof, and, a pharmaceutically suitable carrier vehicle. In an exemplary embodiment, the therapeutically effective dose is in the range of about 36 mg to 36 ng/$kg_{BW}$/day.

BRIEF DESCRIPTION OF DRAWINGS OF THE EXEMPLARY EMBODIMENTS

FIG. 1 is a bar graph showing topical treatment of Rhino mice by topically administering 1α,25-dihydroxy-vitamin $D_3$ (referred to herein as 1,25(OH)$_2D_3$) in a carrier vehicle, whereby the carrier vehicle contained 70 vol. % ethanol and 30 vol. % propylene glycol, whereby the thickness of the epidermis was analyzed after 3 weeks of daily topical administration of 1,25(OH)$_2D_3$, whereby the individual dose was 6 nmole/$kg_{BW}$, and, whereby a very modest increase in epidermal thickness was produced as compared to the vehicle-only control.

Figure 2:
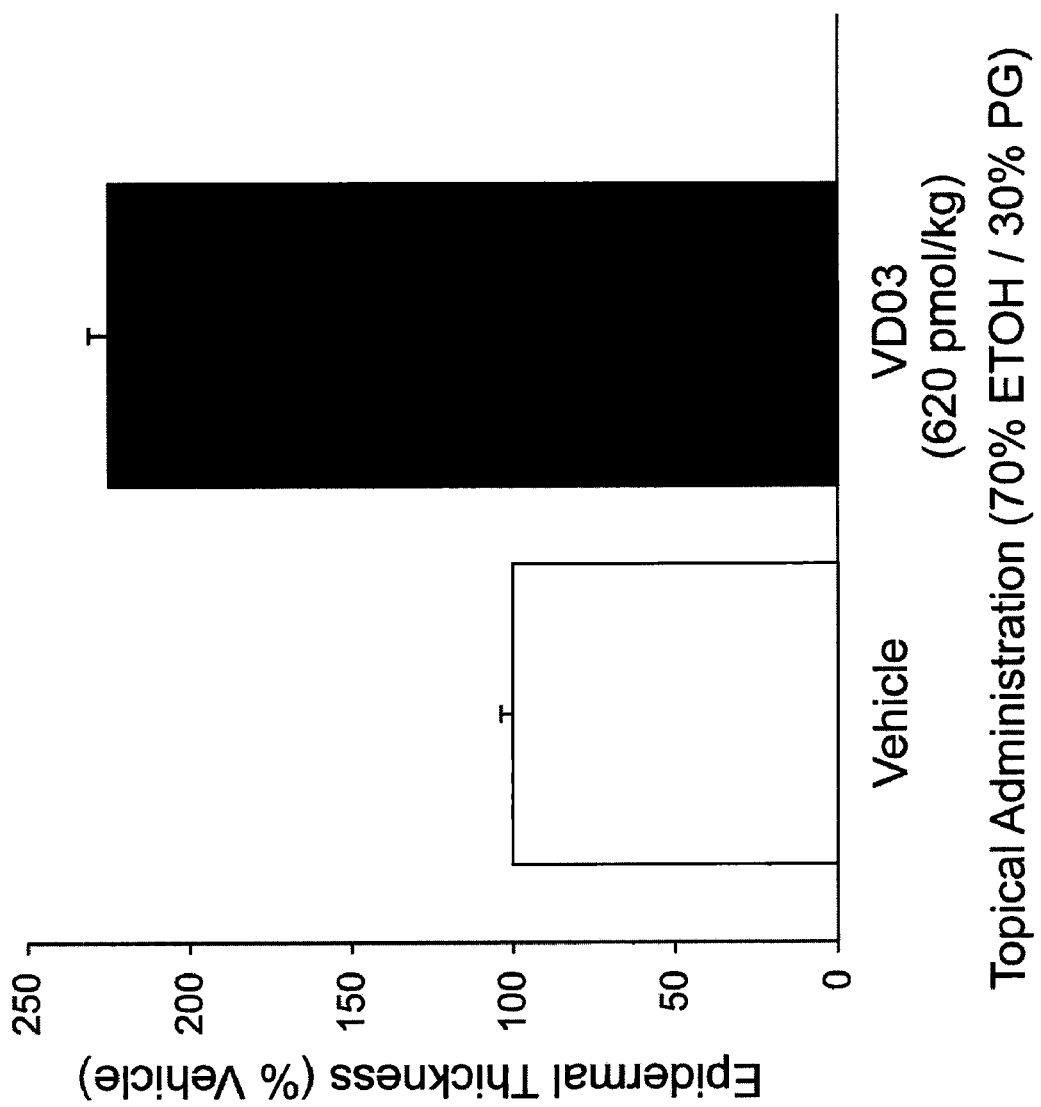

FIG. 2 is a bar graph showing topical treatment of Rhino mice by topically administering 2-methylene-18,19-dinor-(20S)-1α,25-dihydroxyvitamin $D_3$ (referred to herein as VD-03) alone at doses of 620 pmole/$kg_{BW}$/day in a carrier vehicle, whereby the carrier vehicle contained 70 vol. % ethanol and 30 vol. % propylene glycol, and, whereby the epidermal thickness was analyzed after 3 weeks of daily topical administration.

Figure 3:
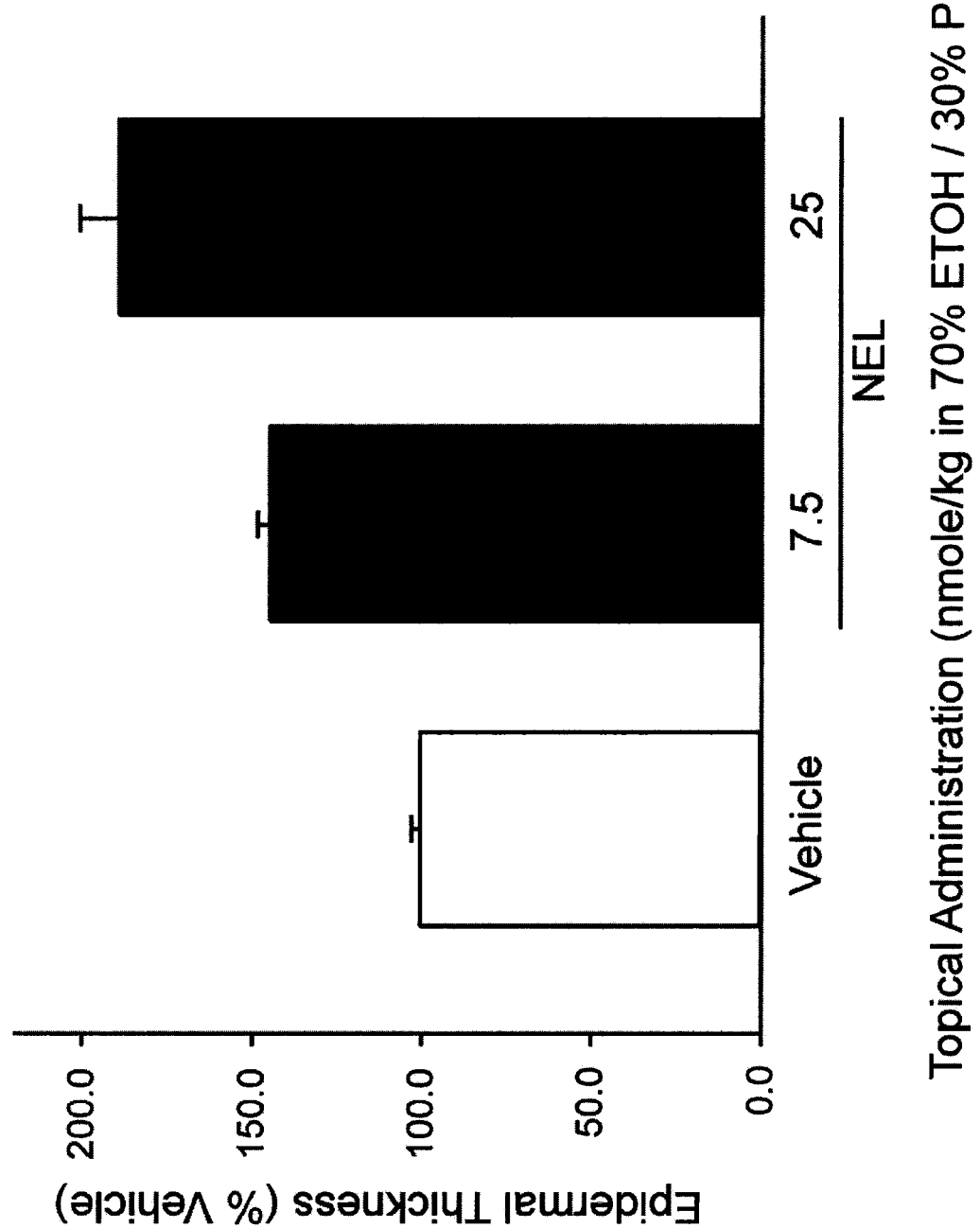

FIG. 3 is a bar graph showing topical treatment of Rhino mice by topically administering 2-methylene-(20R,25S)-19,26-dinor-1α,25-dihydroxyvitamin $D_3$ (referred to herein as NEL) alone at doses of 7.5 nmole/$kg_{BW}$/day and 25 nmole/$kg_{BW}$/day in a carrier vehicle, whereby the carrier vehicle contained 70 vol. % ethanol and 30 vol. % propylene glycol, whereby a dose-dependent increase in epidermal thickness was produced, and, whereby the epidermal thickness was analyzed after 3 weeks of daily topical administration.

Figure 4:
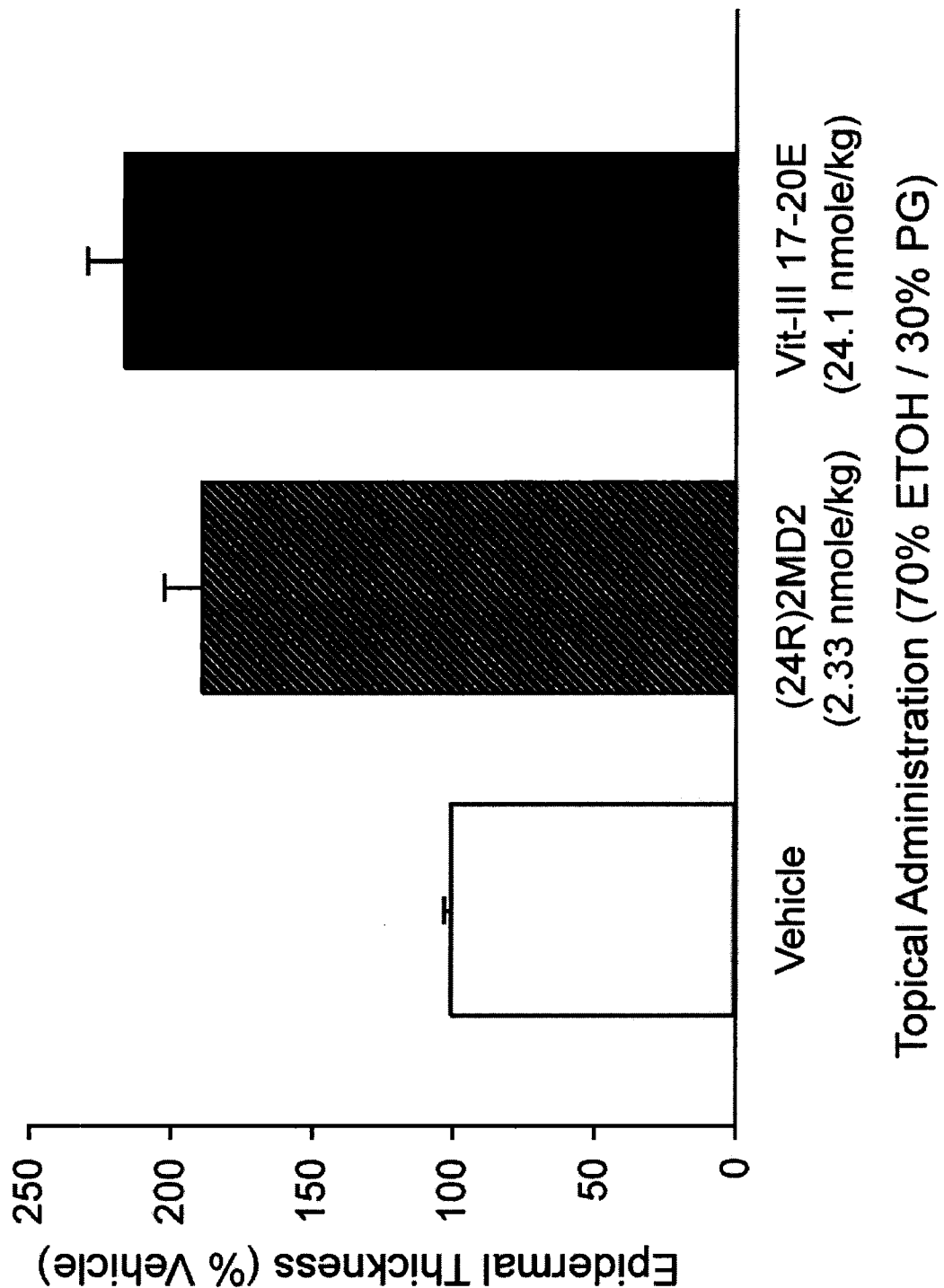

FIG. 4 is a bar graph showing topical treatment of Rhino mice by topically administering 2-methylene-19-nor-(24R)-1α,25-dihydroxyvitamin $D_2$ (herein referred to as (24R) 2MD$_2$) alone at doses of 2.33 nmole/$kg_{BW}$/day in a carrier vehicle, and showing treatment of Rhino mice by administering 2-methylene-1α,25-dihydroxy-(17E)-17(20)-dehydro-19-nor-vitamin $D_3$ (herein referred to as Vit-III (17-20E)) alone at doses of 24.1 nmole/$kg_{BW}$/day in a carrier vehicle, whereby both carrier vehicles contained 70 vol. % ethanol and 30 vol. % propylene glycol, whereby both API-containing formulations and dosage forms produced a significant increase in epidermal thickness as compared to the vehicle control, and, whereby the epidermal thickness was analyzed after 3 weeks of daily topical administration.

Figure 5:
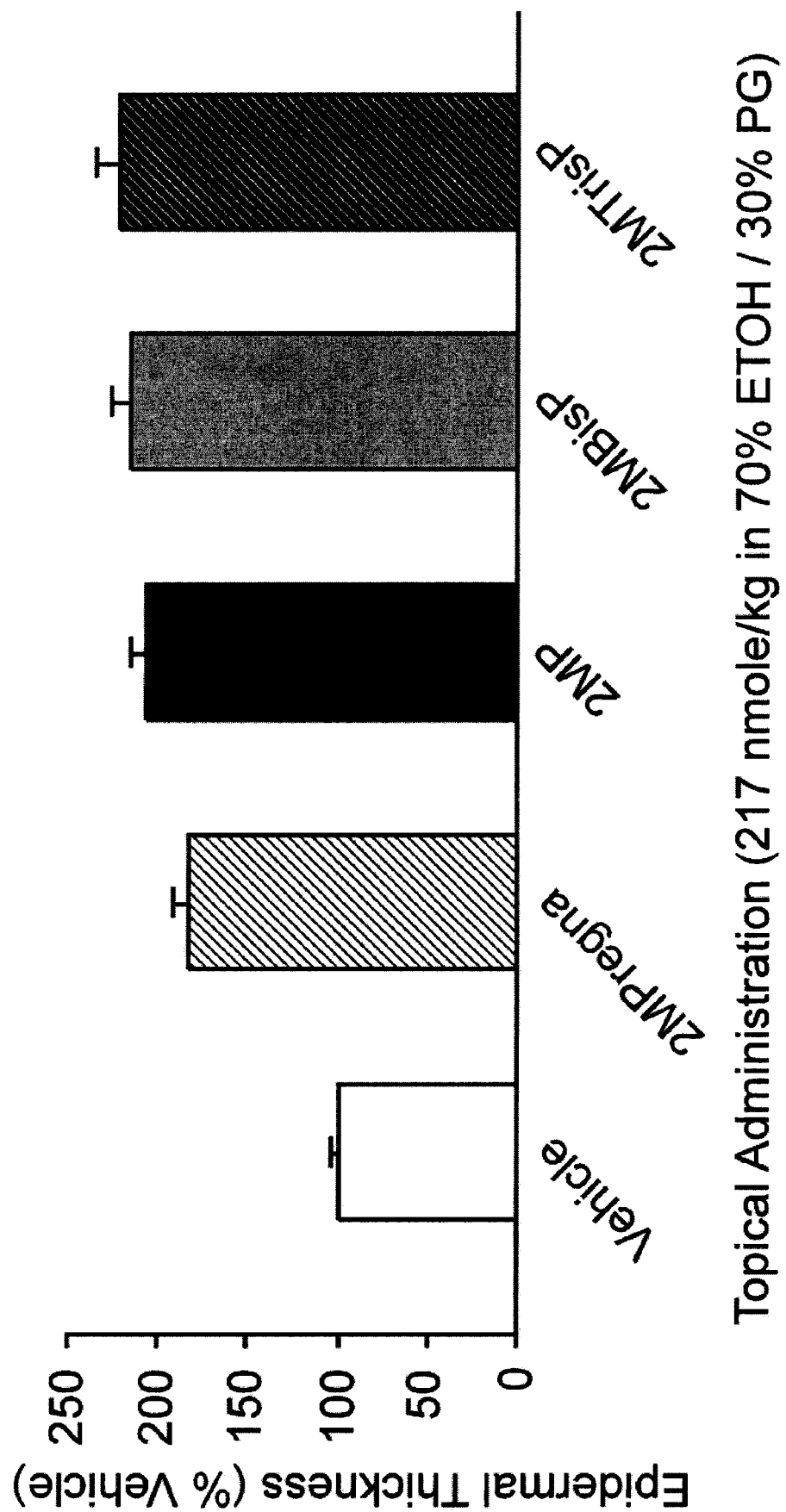

FIG. 5 is a bar graph showing topical treatment of Rhino mice by topically administering 2-methylene-19-nor-1α-hydroxy-pregnacalciferol (referred to herein as 2MPregna) alone, 1α-hydroxy-2-methylene-19-nor-homopregnacalciferol (referred to herein as 2MP) alone, 2-methylene-19-nor-20(S)-1α-hydroxy-bishomopregnacalciferol (referred to herein as 2MBisP) alone, and, 2-methylene-(20S)-19-nor-1α-hydroxy-trishomopregnacalciferol (referred to herein as 2MTrisP) alone each at doses of 217 nmole/$kg_{BW}$/day in a carrier vehicle, whereby both carrier vehicles contained 70 vol. % ethanol and 30 vol. % propylene glycol, whereby each API-containing formulation and dosage form produced a significant increase in epidermal thickness as compared to the control vehicle, and, whereby the epidermal thickness was analyzed after 3 weeks of daily topical administration.

Figure 6:
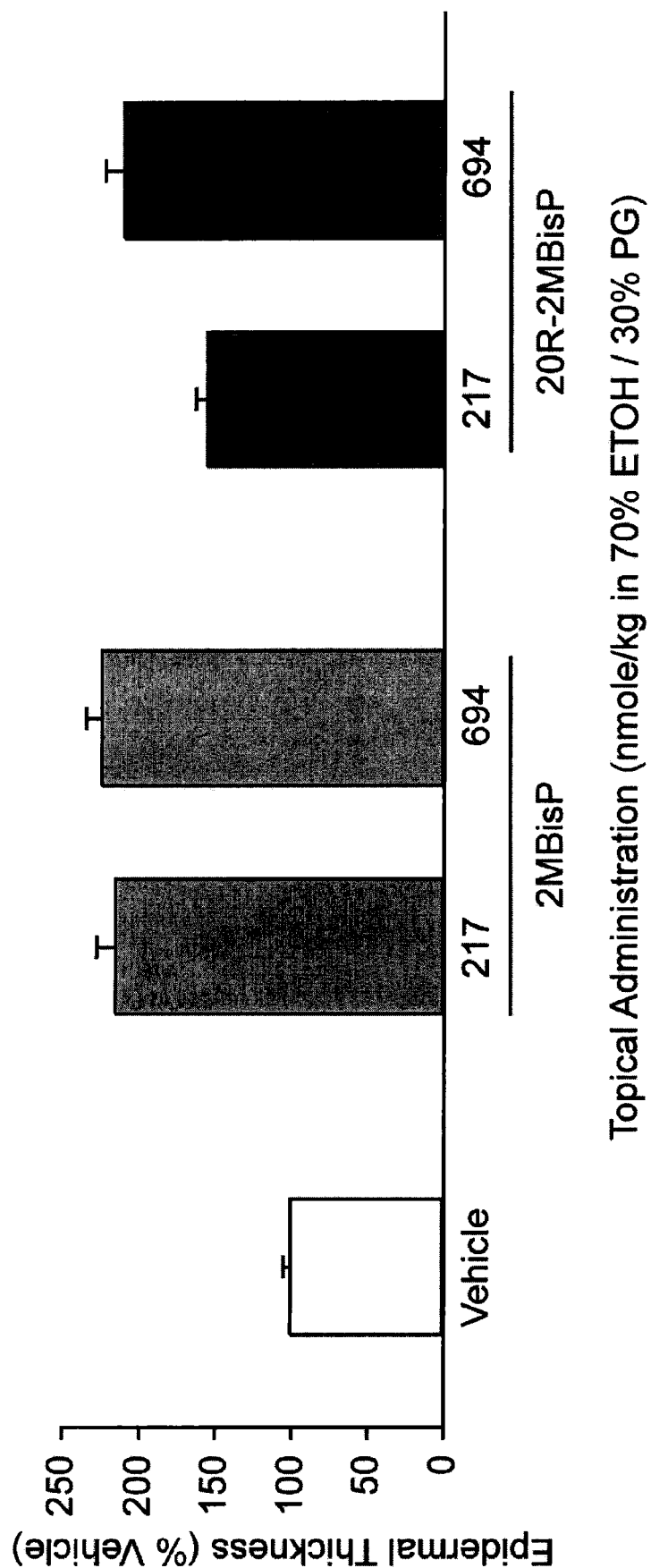

FIG. 6 is a bar graph comparing epidermal thickness of Rhino mice topically treated by administering 2MBisP alone at doses of 217 nmole/$kg_{BW}$/day in a carrier vehicle and 694 nmole/$kg_{BW}$/day in a carrier vehicle, and Rhino mice topically treated by administering (20R)-1α-hydroxy-2-methylene-19-nor-bishomopregnacalciferol (referred to herein as 20R-2MBisP) alone at doses of 217 nmole/$kg_{BW}$/day in a carrier vehicle and 694 nmole/$kg_{BW}$/day in a carrier vehicle (all relative to Rhino mice topically treated with the carrier vehicle alone), whereby each carrier vehicle contained 70 vol. % ethanol and 30 vol. % propylene glycol, whereby epidermal thickness was analyzed after 3 weeks of daily topical treatment, whereby both doses of 2MBisP produced a significant increase in epidermal thickness as compared to the vehicle control, whereby the lower dose of 20R-2MBisP produced some increase in epidermal thickness, whereby the higher dose of 20R-2MBisP produced a significant increase in epidermal thickness, and, whereby the 2MBisP (which has a methyl group in the 20S position) was approximately one-half log more potent than the 20R-2MBisP at increasing epidermal thickness.

Figure 7:
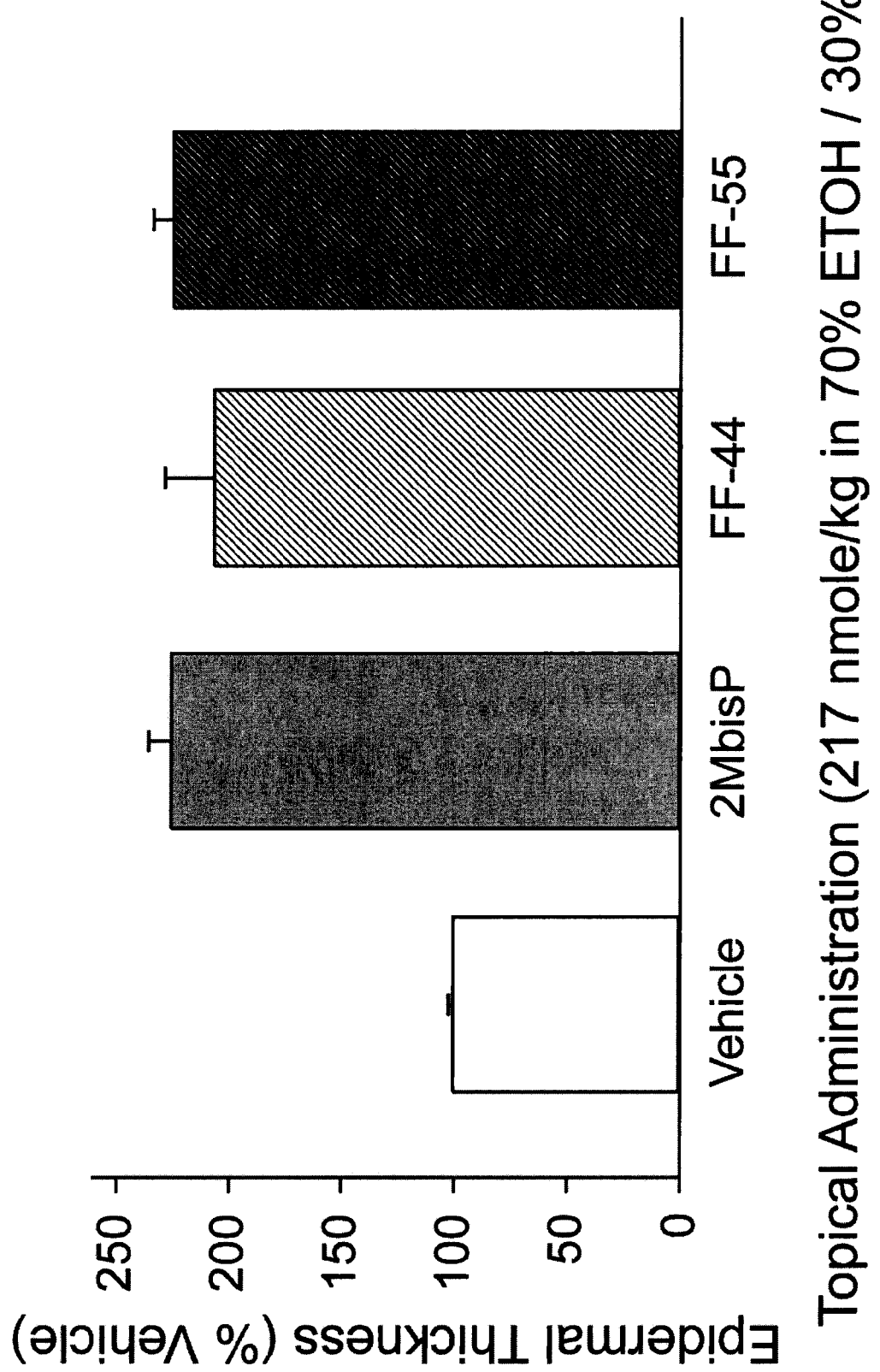

FIG. 7 is a bar graph comparing the epidermal thickness of Rhino mice topically treated by administering 2MBisP alone at doses of 217 nmole/$kg_{BW}$/day in a carrier vehicle, Rhino mice topically treated by administering 2-methylene-(20R)-23,23-difluoro-1α-hydroxy-19-nor-bishomopregnacalciferol (referred to herein as FF-44) alone at doses of 217 nmole/$kg_{BW}$/day in a carrier vehicle, and, Rhino mice topically treated by administering 2-methylene-(20S)-23,23-difluoro-1α-hydroxy-19-nor-bishomopregnancalciferol (referred to herein as FF-55) alone at doses of 217 nmole/$kg_{BW}$/day in a carrier vehicle, whereby each carrier vehicle contained 70 vol. % ethanol and 30 vol. % propylene glycol, whereby the comedone area was analyzed after 3 weeks of daily topical treatment, and, whereby each API-containing formulation and dosage form produced a significant increase in epidermal thickness compared to the vehicle treated group.

Figure 8:
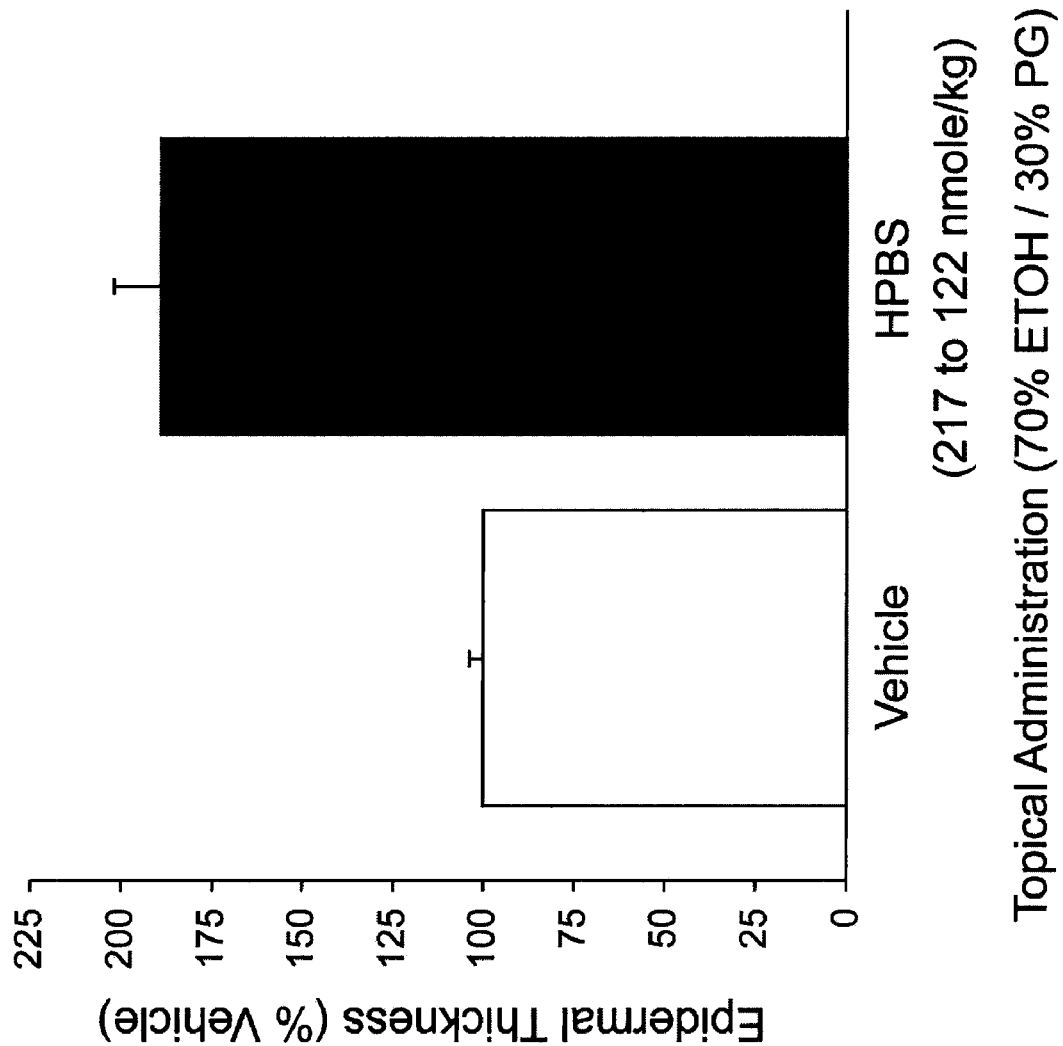

FIG. 8 is a bar graph showing the epidermal thickness of Rhino mice topically treated by administering 2-(3'hydroxypropyl-1',2'-idene)-19,23,24-trinor-(20S)-1α-hydroxyvitamin $D_3$ (referred to herein as HPBS) alone at doses of 217 nmole/$kg_{BW}$/day in a carrier vehicle for 3 days (2 mice) and 10 days (4 mice) followed by lower doses of 122 nmole/$kg_{BW}$/day in a carrier vehicle for the remainder of the study, whereby each carrier vehicle contained 70 vol. % ethanol and 30 vol. % propylene glycol, whereby epidermal thickness was analyzed after 3 weeks of daily topical treatment, and, whereby each API-containing formulation and dosage form produced a significant increase in epidermal thickness as compared to the control vehicle.

Figure 9:
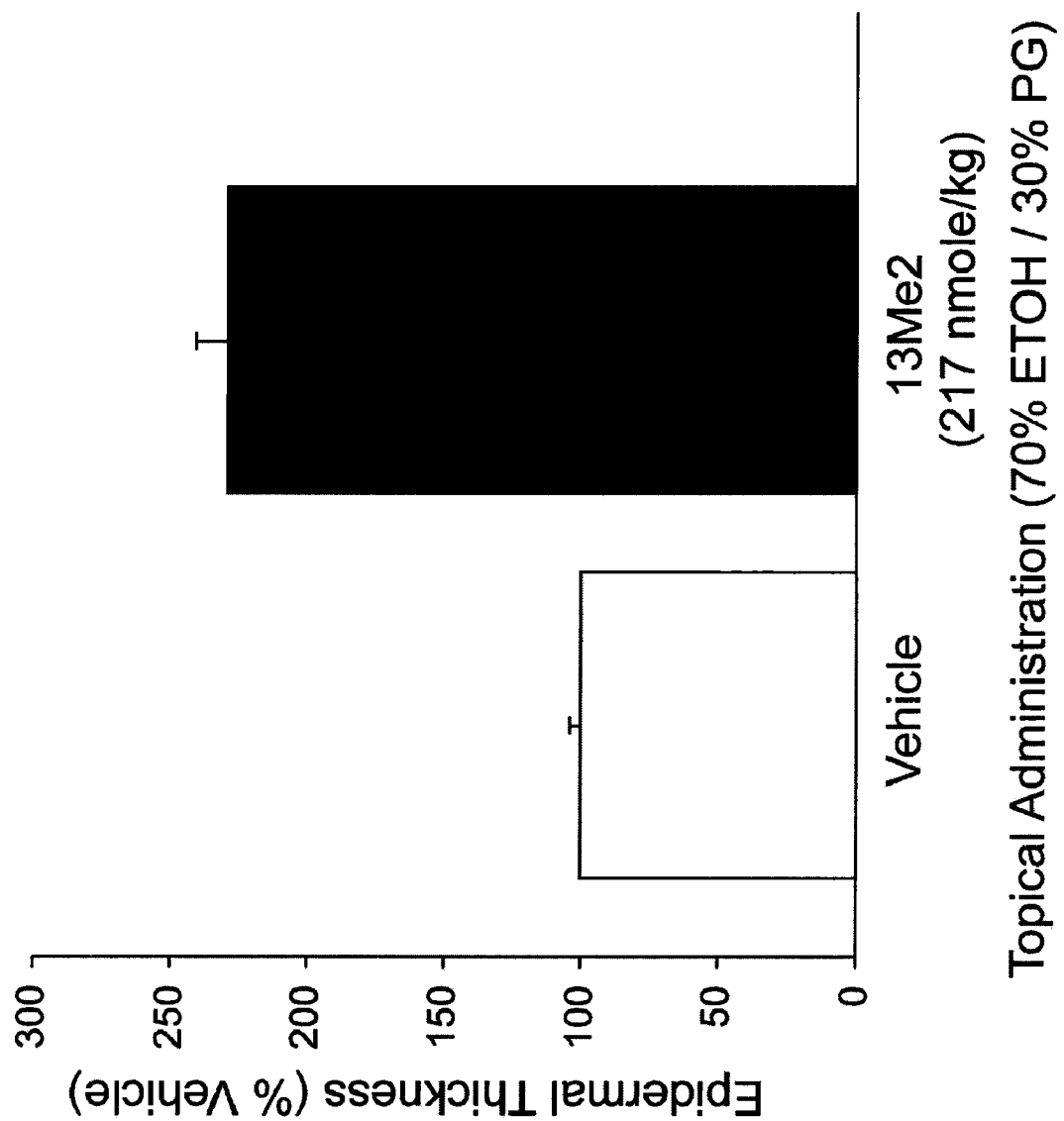

FIG. 9 is a bar graph showing epidermal thickness for Rhino mice topically treated by administering 13,13-dimethyl-des-C,D analog of (20S)-2-methylene-1α,25-dihydroxy-19-nor-vitamin $D_3$ according to the structure

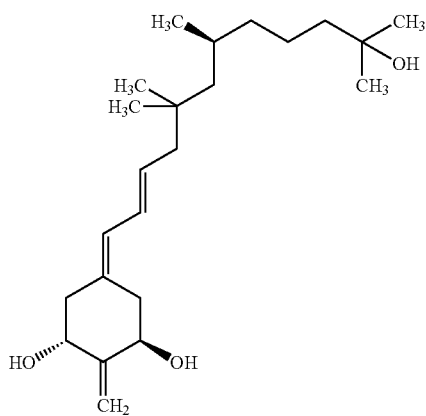

(referred to herein as 13Me₂) alone at doses of 217 nmole/$kg_{BW}$/day in a carrier vehicle, whereby each carrier vehicle contained 70 vol. % ethanol and 30 vol. % propylene glycol, whereby epidermal thickness was analyzed after 3 weeks of daily topical treatment, and, whereby the API-containing formulation and dosage form produced a significant increase in epidermal thickness as compared to the Rhino mice treated with the carrier vehicle.

Figure 10:
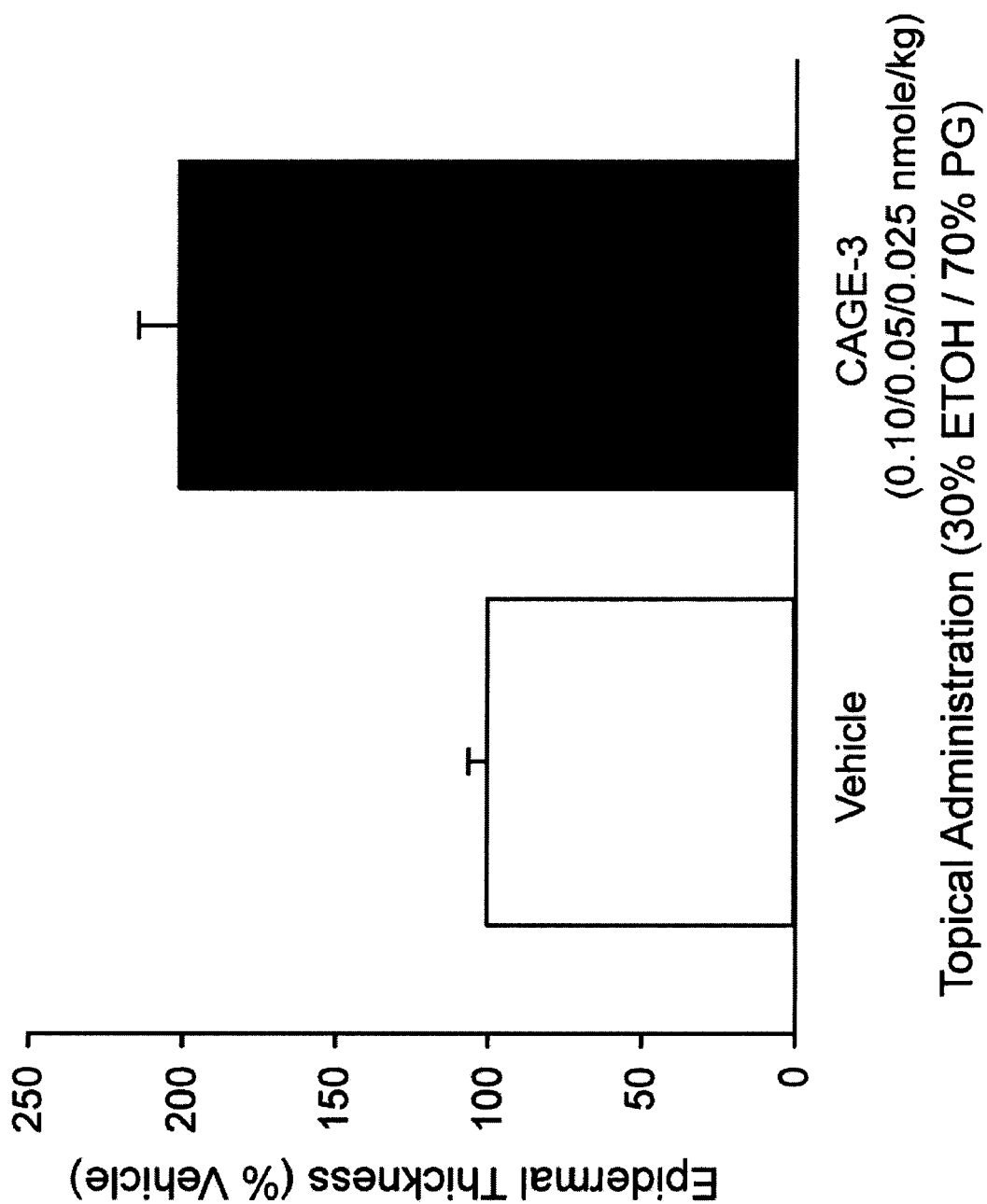

FIG. 10 is a bar graph showing topical treatment of Rhino mice by administering 19-nor-26,27-dimethylene-20(S)-2-methylene-1α,25-dihydroxyvitamin $D_3$ (referred to herein as CAGE-3) alone at initial doses of 0.9 ng/day (ca. 100 picomole/$kg_{BW}$/day followed by reduced doses of 0.45 ng/day beginning on day 10 and 0.22 ng/day (25 picomole/$kg_{BW}$/day) beginning on day 19 (three male mice were not treated on day 19), whereby each dose was in a carrier vehicle that contained 30 vol. % ethanol and 70 vol. % propylene glycol, and, whereby each API-containing formulation and dosage form produced an increase in epidermal thickness as compared to the vehicle control.

Figure 11:
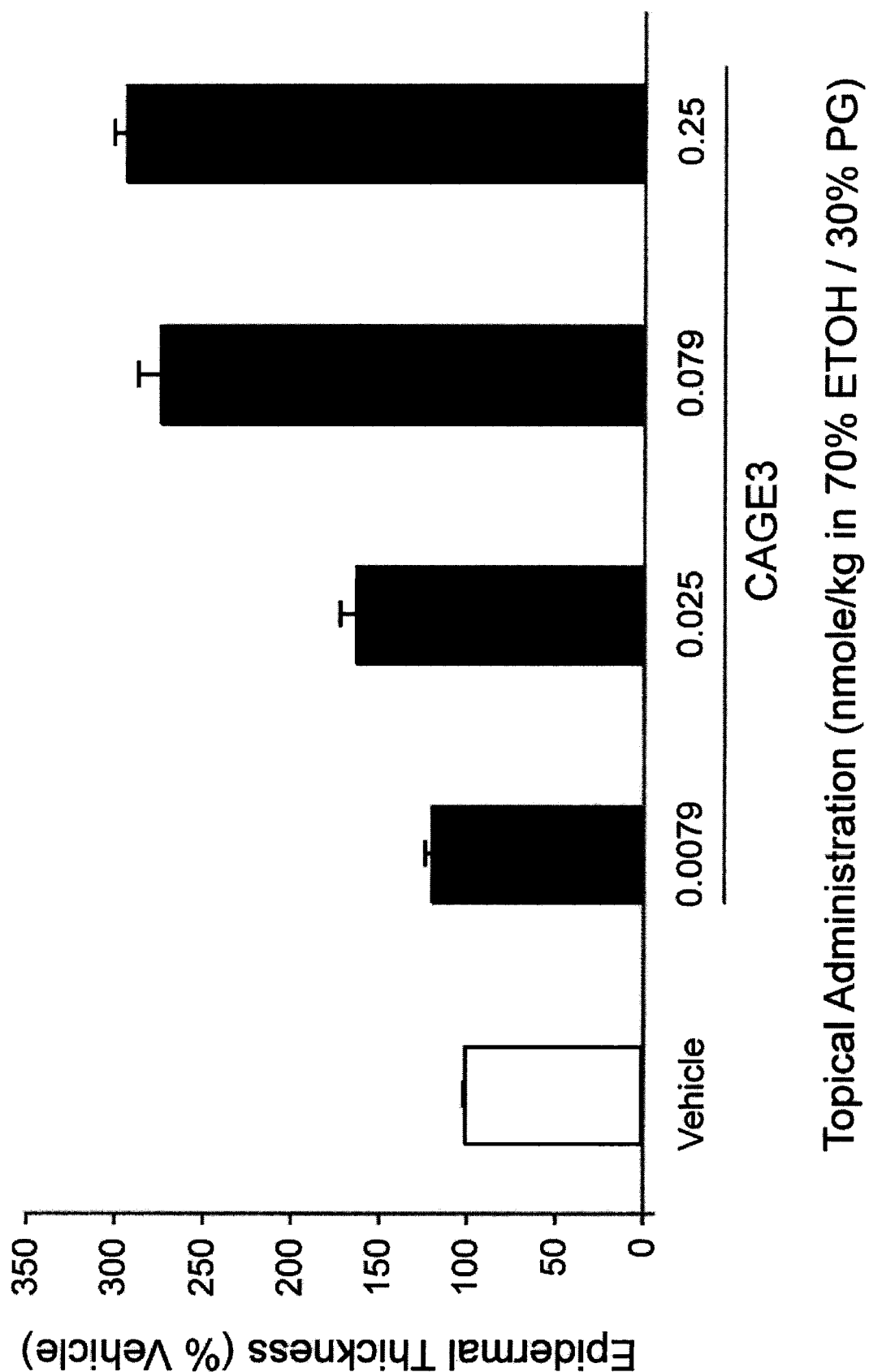

FIG. 11 is a bar graph showing topical treatment of Rhino mice by administering 19-nor-26,27-dimethylene-20(S)-methylene-1α,25-dihydroxyvitamin $D_3$ (referred to herein as CAGE-3) alone at doses of 0.0079 nmol/$kg_{BW}$, 0.025 nmol/$kg_{BW}$, 0.079 nmol/$kg_{BW}$ and 0.25 nmol/$kg_{BW}$ in a carrier vehicle, whereby each carrier vehicle contained 70 vol. % ethanol and 30 vol. % propylene glycol, whereby epidermal thickness was analyzed after 3 weeks of daily topical treatment, whereby the lowest dose of CAGE-3 produced some increase in epidermal thickness compared to the vehicle control, and, whereby the three higher doses of CAGE-3 produced a significant increase in epidermal thickness as compared to the control vehicle.

DERAILED DESCRIPTION OF THE EXEMPLARY EMBODIMENTS

The instant invention is generally directed at methods of increasing the thickness of the epidermal layer in the skin of a human comprising topically administering a therapeutically effective dose of an active pharmaceutical ingredient comprising a vitamin D analog including 2-methylene-19-nor-20(S)-1α-hydroxy-bishomopregnacalciferol, 19-nor-26,27-dimethylene-20(S)-2-methylene-1α,25-dihydroxyvitamin $D_3$, 2-methylene-19-nor-(24R)-1α,25-dihydroxyvitamin $D_2$, 2-methylene-1α,25-dihydroxy-(17E)-17(20)-dehydro-19-nor-vitamin $D_3$, 2-methylene-(20R,25S)-19,26-dinor-1α,25-dihydroxyvitamin $D_3$, 2-methylene-18,19-dinor-(20S)-1α,25-dihydroxyvitamin $D_3$, 2-methylene-19-nor-1α-hydroxypregnacalciferol, 1α-hydroxy-2-methylene-19-nor-homopregnacalciferol, (20R)-1α-hydroxy-2-methylene-19-nor-bishomopregnacalciferol, 2-methylene-(20S)-19-nor-1α-hydroxy-trishomopregnacalciferol, 2-methylene-(20R)-23,23-difluoro-1α-hydroxy-19-nor-bishomopregnacalciferol, 2-methylene-(20S)-23,23-difluoro-1α-hydroxy-19-nor-bishomopregnancalciferol, 2-(3'hydroxypropyl-1',2'-idene)-19,23,24-trinor-(20S)-1α-hydroxyvitamin $D_3$, or 13,13-dimethyl-des-C,D analog of (20S)-2-methylene-1α,25-dihydroxy-19-nor-vitamin $D_3$, and pharmaceutical topical formulations and topical dosage forms thereof using a pharmaceutically suitable carrier vehicle.

The instant invention provides therapeutic active pharmaceutical ingredients, formulations thereof, dosage forms thereof, and method of use thereof to increase epidermal thickness in a mammal, preferably a human. By increasing epidermal thickness, several therapeutic benefits are realized, such as skin barrier function, a reduction in wrinkling, improved wound healing, restoration of the epidermis upon glucocorticoid-induced skin atrophy, and, skin atrophy due to declining hormone (e.g., estrogen and testosterone) levels and/or age and thinning of the skin due to disease.

The active hormonal form of vitamin D, 1,25-dihydroxyvitamin $D_3$ (1,25(OH)$_2$D$_3$), is known to affect cellular proliferation and differentiation. 1,25(OH)$_2$D$_3$ also has immunomodulatory activity.

1,25(OH)$_2$D$_3$ acts by binding to a member of the nuclear receptor super-family being the vitamin D receptor (VDR). The VDR is a ligand-activated transcription factor that (in conjunction with the retinoid X receptor) regulates the transcription of 1,25(OH)$_2$D$_3$ target genes. Skin cells (including keratinocytes, fibroblasts and a number of cells in the immune system that are also present in skin) express VDR.

The vitamin D hormone and analogs have demonstrated therapeutic efficacy in skin diseases involving defective keratinocyte differentiation, such as psoriasis. $1,25(OH)_2D_3$ has been reported to inhibit the proliferation of keratinocytes in culture. (Hosomi et al., 1983, *Endocrinology* 113:1950-1957). $1,25(OH)_2D_3$ may also be effective in treating keratinocyte hyperproliferation and abnormal differentiation in psoriatic patients. Topical administration of $1,25(OH)_2D_3$ to the skin of the hairless C3H mouse has also been reported to induce epidermal proliferation and to increase epidermal thickness. (Gniadecki et al., 1995, *Biochem. Pharmacol.* 49:621-624).

Solutes of the instant vitamin D analog compounds may be made using a pharmaceutically suitable solvent, such as propylene glycol and/or ethanol.

The pharmaceutically suitable topical carrier systems (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

As used herein, the topical dosage form includes various dosage forms known in the art such as lotions (an emulsion, liquid dosage form, whereby this dosage form is generally for external application to the skin), lotion augmented (a lotion dosage form that enhances drug delivery, whereby augmentation does not refer to the strength of the drug in the dosage form), gels (a semisolid dosage form that contains a gelling agent to provide stiffness to a solution or a colloidal dispersion, whereby the gel may contain suspended particles), ointments (a semisolid dosage form, usually containing <20% water and volatiles and >50% hydrocarbons, waxes, or polyols as the vehicle, whereby this dosage form is generally for external application to the skin or mucous membranes), ointment augmented (an ointment dosage form that enhances drug delivery, whereby augmentation does not refer to the strength of the drug in the dosage form), creams (an emulsion, semisolid dosage form, usually containing >20% water and volatiles and/or <50% hydrocarbons, waxes, or polyols as the vehicle, whereby this dosage form is generally for external application to the skin or mucous membranes), cream augmented (a cream dosage form that enhances drug delivery, whereby augmentation does not refer to the strength of the drug in the dosage form), emulsion (a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable, e.g. cream, lotion, ointment), suspensions (a liquid dosage form that contains solid particles dispersed in a liquid vehicle), suspension extended release (a liquid preparation consisting of solid particles dispersed throughout a liquid phase in which the particles are not soluble; the suspension has been formulated in a manner to allow at least a reduction in dosing frequency as compared to that drug presented as a conventional dosage form, e.g., as a solution or a prompt drug-releasing, conventional solid dosage form), pastes (A semisolid dosage form, containing a large proportion, 20-50%, of solids finely dispersed in a fatty vehicle, whereby this dosage form is generally for external application to the skin or mucous membranes), solutions (a clear, homogeneous liquid dosage form that contains one or more chemical substances dissolved in a solvent or mixture of mutually miscible solvents), powders, shampoos (a lotion dosage form which has a soap or detergent that is usually used to clean the hair and scalp; it is often used as a vehicle for dermatologic agents), shampoo suspensions (a liquid soap or detergent containing one or more solid, insoluble substances dispersed in a liquid vehicle that is used to clean the hair and scalp and is often used as a vehicle for dermatologic agents), aerosol foams (i.e., a dosage form containing one or more active ingredients, surfactants, aqueous or nonaqueous liquids, and the propellants; if the propellant is in the internal discontinuous phase, i.e., of the oil-in-water type, a stable foam is discharged, and if the propellant is in the external continuous phase, i.e., of the water-in-oil type, a spray or a quick-breaking foam is discharged), sprays (a liquid minutely divided as by a jet of air or steam), metered spray (a non-pressurized dosage form consisting of valves which allow the dispensing of a specified quantity of spray upon each activation), suspension spray (a liquid preparation containing solid particles dispersed in a liquid vehicle and in the form of coarse droplets or as finely divided solids to be applied locally, most usually to the nasal-pharyngeal tract, or topically to the skin), jellies (a class of gels, which are semisolid systems that consist of suspensions made up of either small inorganic particles or large organic molecules interpenetrated by a liquid--in which the structural coherent matrix contains a high portion of liquid, usually water), films (a thin layer or coating), film extended release (a drug delivery system in the form of a film that releases the drug over an extended period in such a way as to maintain constant drug levels in the blood or target tissue), film soluble (a thin layer or coating which is susceptible to being dissolved when in contact with a liquid), sponges (a porous, interlacing, absorbent material that contains a drug, whereby it is typically used for applying or introducing medication, or for cleansing, and whereby a sponge usually retains its shape), swabs (a small piece of relatively flat absorbent material that contains a drug, whereby a swab may also be attached to one end of a small stick, and whereby a swab is typically used for applying medication or for cleansing), patches (a drug delivery system that often contains an adhesive backing that is usually applied to an external site on the body, whereby its ingredients either passively diffuse from, or are actively transported from, some portion of the patch, whereby depending upon the patch, the ingredients are either delivered to the outer surface of the body or into the body, and whereby a patch is sometimes synonymous with the terms 'extended release film' and 'system'), patch extended release (a drug delivery system in the form of a patch that releases the drug in such a manner that a reduction in dosing frequency compared to that drug presented as a conventional dosage form, e.g., a solution or a prompt drug-releasing, conventional solid dosage form), patch extended release electronically controlled (a drug delivery system in the form of a patch which is controlled by an electric current that releases the drug in such a manner that a reduction in dosing frequency compared to that drug presented as a conventional dosage form, e.g., a solution or a prompt drug-releasing, conventional solid dosage form), and the like. The various topical dosage forms may also be formulated as immediate release, controlled release, sustained release, or the like.

The topical dosage form composition contains an active pharmaceutical ingredient and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, fatty acids, fatty acid esters and polyols), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

The instant invention treats a variety of thin skin conditions by increasing the epidermal thickness of skin. Such causes and conditions of thin skin include: Acrogeria (Gottron Type), Adrenal adenoma, familial, Adrenal Cancer, Adrenal Cortex Diseases, Adrenal Cortex Neoplasms, Adrenal gland hyperfunction, Adrenal incidentaloma, Adrenocortical carcinoma, Aging, Chromosome 22, trisomy, Cockayne syndrome, Connective tissue dysplasia, Spellacy type, Cushing syndrome, familial, Cushing's syndrome, Daentl-Townsend-Siegel syndrome, Daentl-Towsend-Siegel syndrome, Dermoodontodysplasia, Ectodermal dysplasia (mental retardation, central nervous system and malformation, Ectodermal dysplasia (mental retardation, CNS malformation), Ectodermal dysplasia anhidrotic, Ectodermal dysplasia, hypohidrotic, autosomal dominant, Ectodermal dysplasia, hypohidrotic, autosomal recessive, EEC syndrome, Ehilers-Danlos syndrome, Ehlers-Danlos syndrome type IV, Ehlers-Danlos syndrome type VIII, Ehlers-Danlos syndrome type X, Ehlers-Danlos syndrome, cardiac valvular form, Ehlers-Danlos syndrome, vascular type, Epidermolysis bullosa, junctional, Fontaine-Farriaux-Blanckaert syndrome, Frohlich syndrome, Functioning pancreatic endocrine tumor, Geroderma osteodysplastica, Goltz syndrome, Homocystinuria, Hutchinson Gilford Syndrome, Hyperadrenalism, Jones-Hersh-Yusk syndrome, Lamellar ichthyosis, Lamellar ichthyosis, autosomal dominant form, Lamellar ichthyosis, type 1, Lamellar ichthyosis, type 2, Lamellar ichthyosis, type 3, Lenz Majewski hyperostotic dwarfism, Mental retardation (arachnodactyly, hypotonia and telangiectasia), Myopathy, limb-girdle, with bone fragility, Neu-Laxova Syndrome, OLE-DAID, Onychotrichodysplasia and neutropenia, Osteogenesis imperfecta, Osteogenesis imperfecta Type I, Osteogenesis imperfecta, type 1A, Osteogenesis imperfecta, type 1B, Osteogenesis imperfecta, type 2, Osteogenesis imperfecta, type 2A, Osteogenesis imperfecta, type 4, Osteogenesis imperfecta, type IIB, Peptidic growth factors deficiency, Pituitary cancer, childhood, Pituitary tumors, adult, Poikilodermatomyositis—mental retardation, Progeria, Progeria short stature pigmented nevi, Pseudoprogeria syndrome, Rambaud-Galian syndrome, Rapp-Hodgkin syndrome, Rombo syndrome, Sequeiros-Sack syndrome, Shprintzen-Golberg craniosynostosis, Spastic paraplegia (neuropathy, poikiloderma), Stoll-Alembik-Finck syndrome, and, Tricho odonto onycho dermal syndrome.

EXAMPLES

Table 1 demonstrates the effect of $1,25(OH)_2D_3$ and various vitamin D analogs on epidermal thickness by summarizing increased epidermal thickness as a percentage of vehicle-only treated skin.

TABLE 1

| Vitamin D Analog* | API-Treated Epidermal Thickness (% Vehicle) | Topical API Dose (nmol/kg) | N |
|---|---|---|---|
| $1,25(OH)_2D_3$ | 118 ± 7 | 6.0 | 6 |
| VD-03 | 225 ± 6 | 0.62 | 6 |
| NEL | 145 ± 4 | 7.5 | 6 |
| NEL | 189 ± 11 | 25 | 6 |
| Vit-III 17-20E | 216 ± 13 | 24 | 6 |
| $(24R)2MD_2$ | 189 ± 13 | 2.3 | 6 |
| 2MPregna | 183 ± 8 | 217 | 6 |
| 2MP | 207 ± 8 | 217 | 6 |
| 2MBisP | 220 ± 8 | 217 | 12 |
| 2MBisP | 231 ± 6 | 694 | 12 |
| 20R-2MBisP | 155 ± 7 | 217 | 6 |
| 20R-2MBisP | 209 ± 13 | 694 | 6 |
| 2MTrisP | 221 ± 15 | 217 | 6 |
| FF-44 | 206 ± 22 | 217 | 6 |
| FF-55 | 225 ± 9 | 217 | 6 |
| HPBS | 189 ± 13 | 217 to 122** | 6 |
| 13Me2 | 229 ± 12 | 217 | 6 |
| CAGE-3 | 162 ± 11 | 0.025 | 5 |
| CAGE-3 | 274 ± 14 | 0.079 | 6 |
| CAGE-3 | 293 ± 8 | 0.25 | 6 |

*All compounds were applied topically on a daily basis in a carrier vehicle comprised of 70% ethanol and 30% propylene glycol.
**Dose changed as indicated on day 10 of the experiment.

The predictive dosing ranges set forth in Table 2 were calculated with the following assumption. For the high end of the oral dose range, the highest dose given to the Rhino mouse has been corrected for the expected lesser sensitivity of a human, and the dose has been further increased by 0.5 log dose. The low dose is $1 \times 10^6$ lower than the high dose. Regarding the high end topical dose, the value has been further multiplied by a factor of 20 because humans absorb only about 5% of the API as compared to 100% in mice allowing for higher exposure in the human before toxicity would be anticipated to occur. Differences in animal species skin sensitivity and relative skin absorption concerning various vitamin D analogs may also significantly affect the predictive efficacious dose in humans.

Table 2 provides exemplary predictive human topical dosing ranges of API.

TABLE 2

| Vitamin D Analog | Predictive Exemplary Topical Dosing of API in Humans |
|---|---|
| 2MBisP | 340 mg to 0.34 µg/$kg_{BW}$/day |
| CAGE-3 | 14 µg to 14 pg/$kg_{BW}$/day |
| $24R-2MD_2$ | 450 µg to 0.45 ng/$kg_{BW}$/day |
| VitIII (17-20E) | 4.5 mg to 4.5 ng/$kg_{BW}$/day |
| NEL | 4.5 mg to 4.5 ng/$kg_{BW}$/day |
| VD-03 | 11 µg to 0.11 ng/$kg_{BW}$/day |
| 2MPregna | 340 mg to 0.34 µg/$kg_{BW}$/day |
| 2MP | 340 mg to 0.34 µg/$kg_{BW}$/day |
| 20R-2MBisP | 340 mg to 0.34 µg/$kg_{BW}$/day |
| 2MTrisP | 34 mg to 34 ng/$kg_{BW}$/day |
| FF-44 | 340 mg to 0.34 µg/$kg_{BW}$/day |
| FF-55 | 340 mg to 0.34 µg/$kg_{BW}$/day |
| HPBS | 41 mg to 41 ng/$kg_{BW}$/day |
| 13Me2 | 36 mg to 36 ng/$kg_{BW}$/day |

Methods. Animals and dose administration. Rhino mice 6-8 weeks old were dosed daily via the topical route. The mice were weighed three times per week. Doses of API were adjusted weekly based on body weight. The topical formulations dosage forms were made by mixing the API with two different topical carriers. One topical carrier consisted of 70 vol % propylene glycol and 30 vol % ethanol. The other topical carrier consisted of 30 vol % propylene glycol and 70 vol % ethanol. The topical vehicle control for a given comparative example was the vehicle carrier used in the API-formulated topical dosage form. Animals were euthanized 72 hours after administration of the final topical dose, and dorsal skin was collected for histological analysis.

Measurement of epidermal thickness. The extent of the efficacious increase in epidermal thickness was assessed by measuring the thickness (i.e., depth) of the epidermal layer of the skin. The degree of increase in epidermal thickness (as compared to the increase in epidermal thickness in carrier vehicle-only treated skin) was indicative of the degree of efficacy.

Epidermal thickness was determined by histological analysis of tissue sections. Skin was fixed overnight in 4% paraformaldehyde at 4° C. with gentle agitation. The skin was dehydrated the following day in 100% methanol. Samples were embedded in paraffin. Nine sections, each measuring 10 μm and each separated by 150 μm, were taken from each mouse and stained with hematoxylin and eosin stain. Five of the nine sections were digitally imaged (6× magnification) for analysis of the epidermal thickness using Metamorph Imaging Software (single line function).

The thickness of the epidermis adjacent to each comedone (open or healed) on each respective image of the five sections was also then measured using a Wacom Intuos 3 Graphics Tablet interfaced with the software. The average width was determined for each Rhino mouse from multiple measurements. Individual epidermal thickness average was determined from a composite of measurements taken from all 5 images. Such average for each mouse was used to calculate the treatment group mean. Results in the figures are expressed in terms of mean±standard error of the mean.

Preparation of topical formulations and dosage forms containing the various API's including 2MBis P, CAGE-3, 24R-2MD$_2$, VitIII (17-20E), NEL, VD-03, 2MPregna, 2MP, 20R-2MBisP, 2MTrisP, FF-44, FF-55, HPBS and 13Me2. Separate concentrated ethanolic stock solutions of each API were diluted to a predetermined dose concentration using a topical carrier vehicle. Two different carrier vehicles were used. One topical carrier consisted of 70 vol % propylene glycol and 30 vol % ethanol. The other topical carrier consisted of 30 vol % propylene glycol and 70 vol % ethanol. The vehicle was thoroughly mixed with the API. The topical dosing formulation and dosage form delivered a predetermined amount of API on a per kilogram body weight basis.

A 100 μL dose was administered to the back of the mouse. An average weight of 24-30 g/mouse was assumed initially in the dose volume calculations. Dosing volumes were adjusted weekly to deliver the predetermined desired dose amount of API based on the body weight of each animal.

We claim:
1. A method of increasing the thickness of the epidermal layer in the skin of a human comprising topically administering a therapeutically effective dose of an active pharmaceutical ingredient selected from the group consisting of:

2-methylene-19-nor-20(S)-1α-hydroxy-bishomopregnacalciferol according to the structure

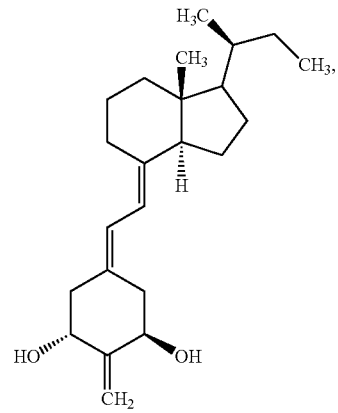

19-nor-26,27-dimethylene-20(S)-2-methylene-1α,25-dihydroxyvitamin D$_3$ according to the structure

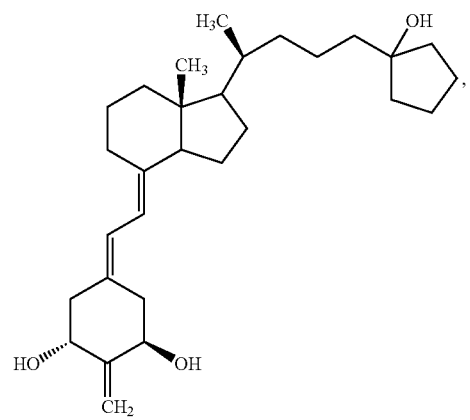

2-methylene-19-nor-(24R)-1α,25-dihydroxyvitamin D$_2$ according to the structure

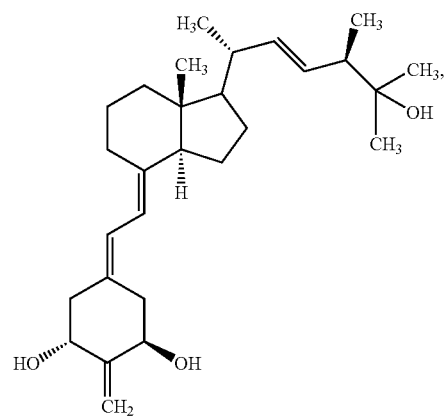

25

2-methylene-1α,25-dihydroxy-(17E)-17(20)-dehydro-
19-nor-vitamin D₃ according to the structure

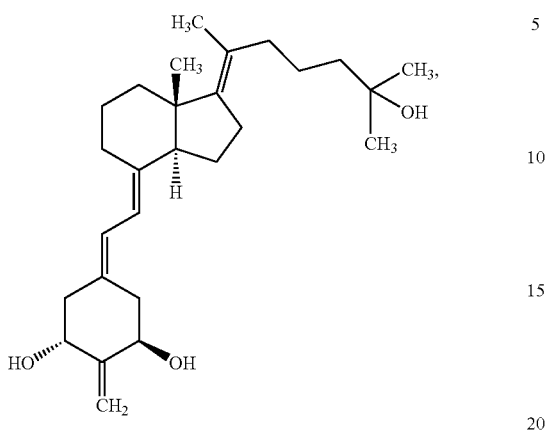

2-methylene-(20R,25S)-19,26-dinor-1α,25-dihydroxyvi-
tamin D₃ according to the structure

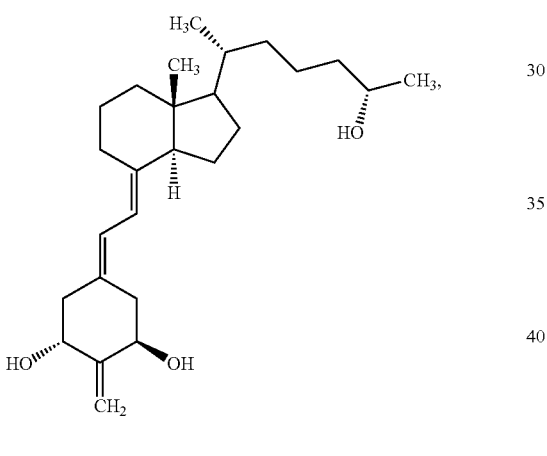

2-methylene-18,19-dinor-(20S)-1α,25-dihydroxyvitamin
D₃ according to the structure

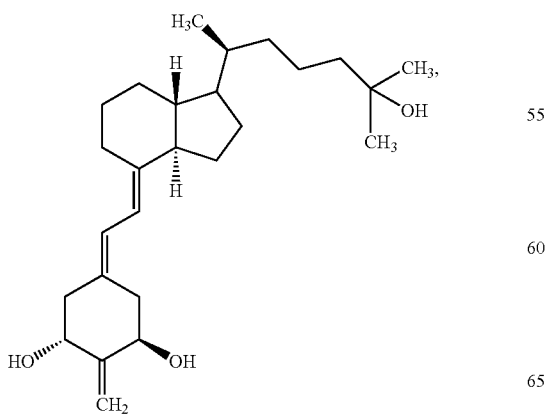

26

2-methylene-19-nor-1α-hydroxy-pregnacalciferol
according to the structure

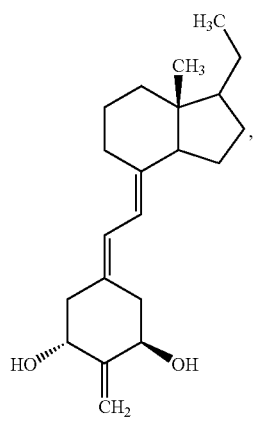

1α-hydroxy-2-methylene-19-nor-homopregnacalciferol
according to the structure

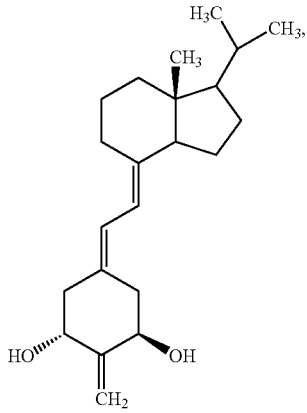

(20R)-1α-hydroxy-2-methylene-19-nor-bishomopregna-
calciferol according to the structure

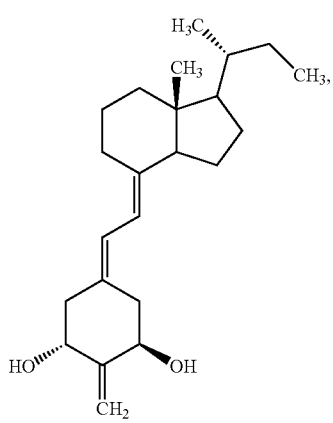

2-methylene-(20S)-19-nor-1α-hydroxy-trishomopregna-calciferol according to the structure

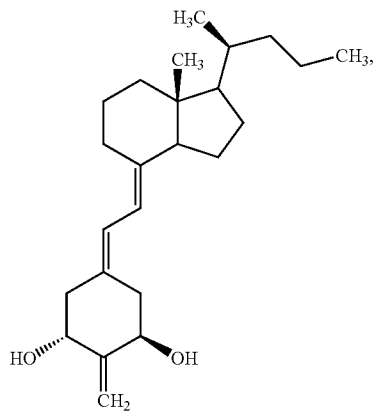

2-methylene-(20R)-23,23-difluoro-1α-hydroxy-19-nor-bishomopregnacalciferol according to the structure

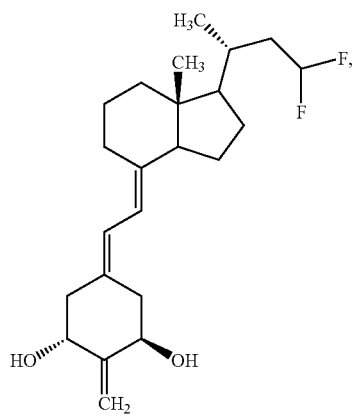

2-methylene-(20S)-23,23-difluoro-1α-hydroxy-19-nor-bishomopregnancalciferol according to the structure

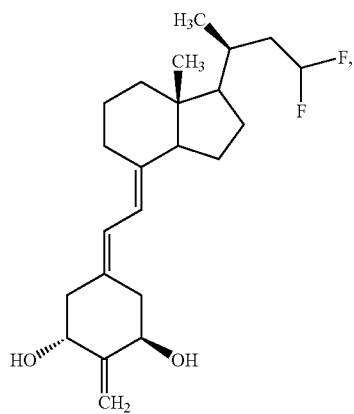

2-(3'hydroxypropyl-1',2'-idene)-19,23,24-trinor-(20S)-1α-hydroxyvitamin $D_3$ according to the structure

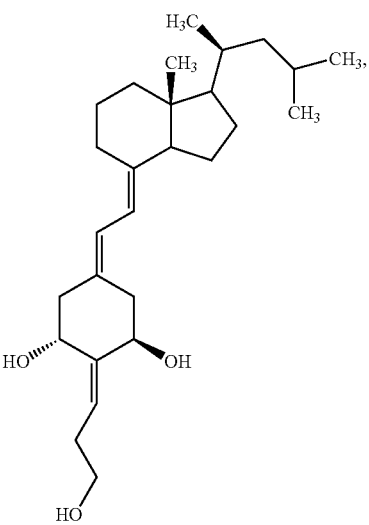

13,13-dimethyl-des-C,D analog of (20S)-2-methylene-1α,25-dihydroxy-19-nor-vitamin $D_3$ according to the structure

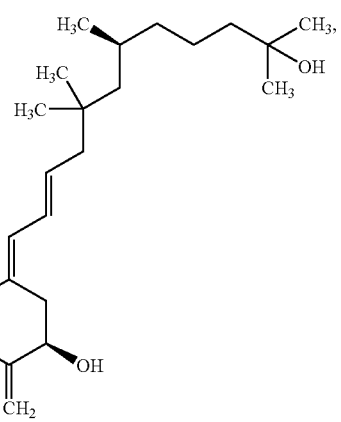

or, a stereoisomer thereof.

2. The method of claim 1 comprising topically administering the therapeutically effective dose of the 2-methylene-19-nor-20(S)-1α-hydroxy-bishomopregnacalciferol according to the structure

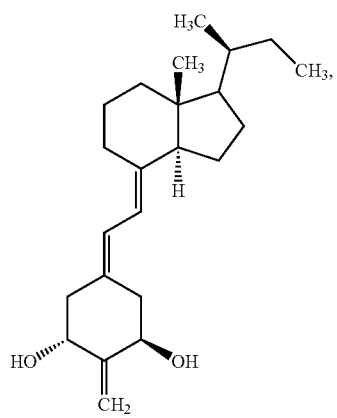

or, a stereoisomer thereof.

3. The method of claim 2, wherein the therapeutically effective dose is in the range of about 340 mg to 0.34 µg/kg$_{BW}$/day.

4. The method of claim 1 comprising topically administering the therapeutically effective dose of the 19-nor-26,27-dimethylene-20(S)-2-methylene-1α,25-dihydroxyvitamin D$_3$ according to the structure

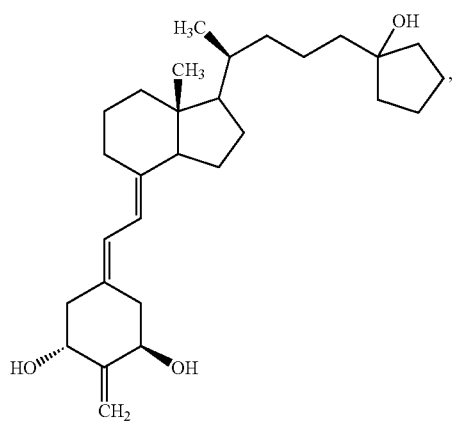

or, a stereoisomer thereof.

5. The method of claim 4, wherein the therapeutically effective dose is in the range of about 14 µg to 14 pg/kg$_{BW}$/day.

6. The method of claim 1 comprising topically administering the therapeutically effective dose of the 2-methylene-19-nor-(24R)-1α,25-dihydroxyvitamin D$_2$ according to the structure

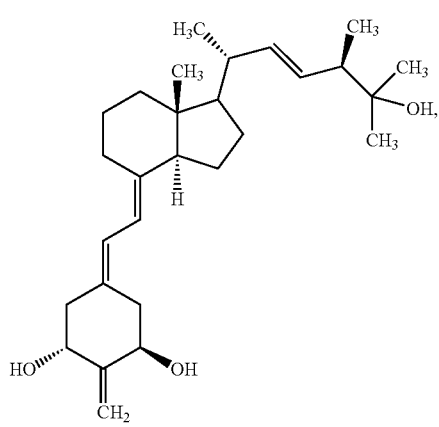

or, a stereoisomer thereof

7. The method of claim 6, wherein the therapeutically effective dose is in the range of about 450 µg to 0.45 ng/kg$_{BW}$/day.

8. The method of claim 1 comprising topically administering the therapeutically effective dose of the 2-methylene-1α, 25-dihydroxy-(17E)-17(20)-dehydro-19-nor-vitamin D$_3$ according to the structure

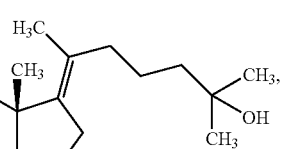

or, a stereoisomer thereof.

9. The method of claim 8, wherein the therapeutically effective dose is in the range of about 4.5 mg to 4.5 ng/kg$_{BW}$/day.

10. The method of claim 1 comprising topically administering the therapeutically effective dose of the 2-methylene-(20R,25S)-19,26-dinor-1α,25-dihydroxyvitamin D$_3$ according to the structure

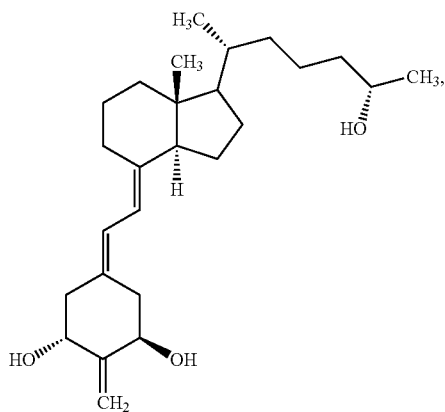

or, a stereoisomer thereof.

11. The method of claim 10, wherein the therapeutically effective dose is in the range of about 4.5 mg to 4.5 ng/kg$_{BW}$/day.

12. The method of claim 1 comprising topically administering the therapeutically effective dose of the 2-methylene-18,19-dinor-(20S)-1α,25-dihydroxyvitamin D$_3$ according to the structure

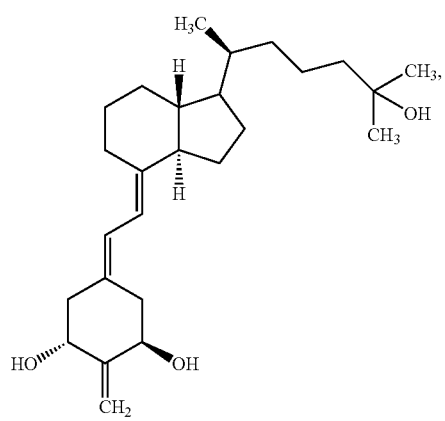

or, a stereoisomer thereof.

13. The method of claim 12, wherein the therapeutically effective dose is in the range of about 11 μg to 0.11 ng/kg$_{BW}$/day.

14. The method of claim 1 comprising topically administering the therapeutically effective dose of the 2-methylene-19-nor-1α-hydroxy-pregnacalciferol according to the structure

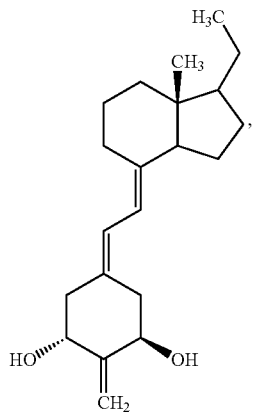

or, a stereoisomer thereof.

15. The method of claim 14, wherein the therapeutically effective dose is in the range of about 340 mg to 0.34 μg/kg$_{BW}$/day.

16. The method of claim 1 comprising topically administering the therapeutically effective dose of the 1α-hydroxy-2-methylene-19-nor-homopregnacalciferol according to the structure

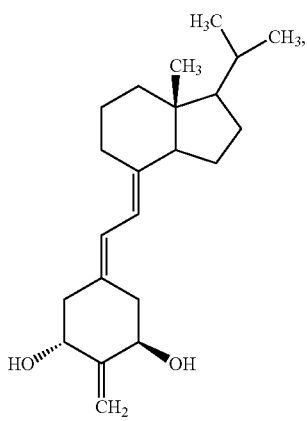

or, a stereoisomer thereof.

17. The method of claim 16, wherein the therapeutically effective dose is in the range of about 340 mg to 0.34 μg/kg$_{BW}$/day.

18. The method of claim 1 comprising topically administering the therapeutically effective dose of the (20R)-1α-hydroxy-2-methylene-19-nor-bishomopregnacalciferol according to the structure

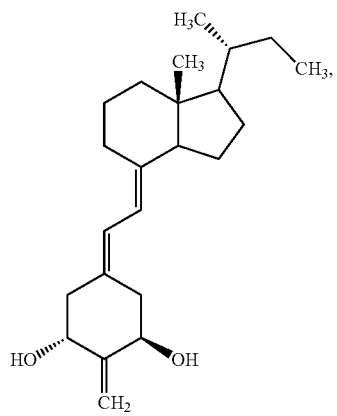

or, a stereoisomer thereof.

19. The method of claim 18, wherein the therapeutically effective dose is in the range of about 340 mg to 0.34 μg/kg$_{BW}$/day.

20. The method of claim 1 comprising topically administering the therapeutically effective dose of the 2-methylene-(20S)-19-nor-1α-hydroxy-trishomopregnacalciferol according to the structure

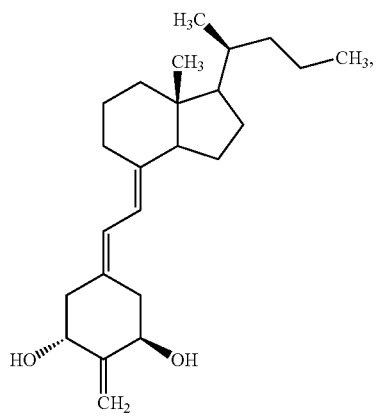

or, a stereoisomer thereof.

21. The method of claim 20, wherein the therapeutically effective dose is in the range of about 34 mg to 34 ng/kg$_{BW}$/day.

22. The method of claim 1 comprising topically administering the therapeutically effective dose of the 2-methylene-(20R)-23,23-difluoro-1α-hydroxy-19-nor-bishomopregnacalciferol according to the structure

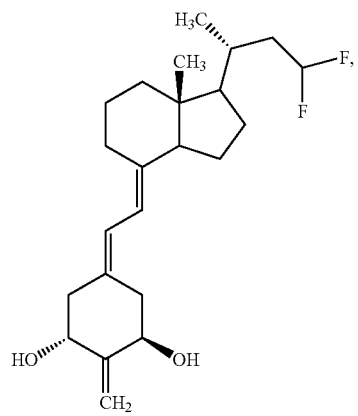

or, a stereoisomer thereof.

23. The method of claim 22, wherein the therapeutically effective dose is in the range of about 340 mg to 0.34 μg/kg$_{BW}$/day.

24. The method of claim 1 comprising topically administering the therapeutically effective dose of the 2-methylene-(20S)-23,23-difluoro-1α-hydroxy-19-nor-bishomopregnancalciferol according to the structure

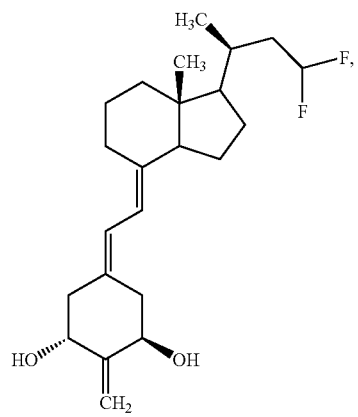

or, a stereoisomer thereof.

25. The method of claim 24, wherein the therapeutically effective dose is in the range of about 340 mg to 0.34 μg/kg$_{BW}$/day.

26. The method of claim 1 comprising topically administering the therapeutically effective dose of the 2-(3'hydroxypropyl-1',2'-idene)-19,23,24-trinor-(20S)-1α-hydroxyvitamin D$_3$ according to the structure

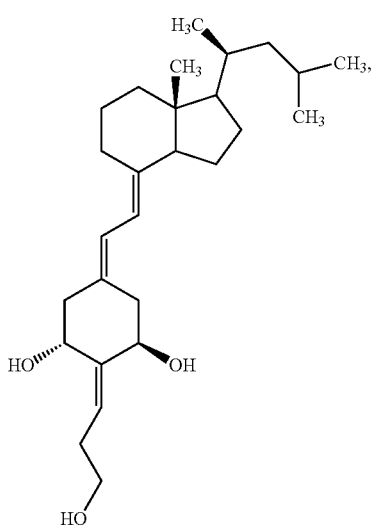

or, a stereoisomer thereof.

27. The method of claim 26, wherein the therapeutically effective dose is in the range of about 41 mg to 41 ng/kg$_{BW}$/day.

28. The method of claim 1 comprising topically administering the therapeutically effective dose of the 13,13-dimethyl-des-C,D analog of (20S)-2-methylene-1α,25-dihydroxy-19-nor-vitamin D$_3$ according to the structure

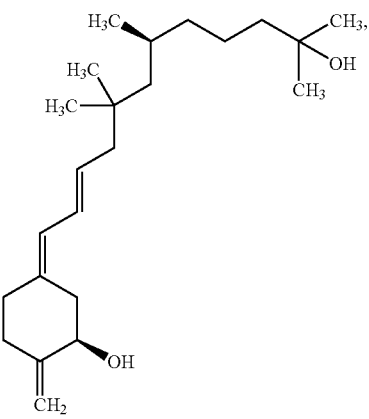

or, a stereoisomer thereof.

29. The method of claim 28, wherein the therapeutically effective dose is in the range of about 36 mg to 36 ng/kg$_{BW}$/day.

\* \* \* \* \*

UNITED STATES PATENT AND TRADEMARK OFFICE
CERTIFICATE OF CORRECTION

PATENT NO.        : 8,143,238 B2           Page 1 of 1
APPLICATION NO.   : 12/399070
DATED             : March 27, 2012
INVENTOR(S)       : DeLuca et al.

It is certified that error appears in the above-identified patent and that said Letters Patent is hereby corrected as shown below:

Column 21, line 38 "Ehilers" should be --Ehlers--

Signed and Sealed this
Twenty-ninth Day of May, 2012

David J. Kappos
*Director of the United States Patent and Trademark Office*